United States Patent [19]

Kamano et al.

[11] Patent Number: 4,567,172
[45] Date of Patent: Jan. 28, 1986

[54] 6α-METHYLPREDNISOLONE DERIVATIVES

[75] Inventors: Yoshiaki Kamano, Tempe, Ariz.; Saburo Sugai, Saitama, Japan; Tokuji Okazaki, Tokyo, Japan; Seiichiro Yoshida, Tokyo, Japan; Sanya Akaboshi, Tokyo, Japan

[73] Assignee: Ohta Seiyaku Kabushiki Kaisha, Tokyo, Japan

[21] Appl. No.: 498,636

[22] Filed: May 27, 1983

[30] Foreign Application Priority Data

May 31, 1982 [JP] Japan .................................. 57-91389
Jul. 2, 1982 [JP] Japan .................................. 57-114011
Apr. 15, 1983 [JP] Japan .................................. 58-66872

[51] Int. Cl.$^4$ ............................................ A61K 31/56
[52] U.S. Cl. ............................... 514/179; 260/397.45; 260/239.55 D
[58] Field of Search ................. 260/397.45; 424/243

[56] References Cited

U.S. PATENT DOCUMENTS

| | | | |
|---|---|---|---|
| 3,312,590 | 4/1967 | Elks et al. | 260/397.45 |
| 4,343,799 | 8/1982 | Heckler | 424/243 |
| 4,358,445 | 11/1982 | MacDonald | 424/243 |
| 4,435,390 | 3/1984 | Annen et al. | 260/397.45 |

OTHER PUBLICATIONS

Chemical Abstracts 99(5), Par. 38,713s, Abstract of Eur. Pat. Appl. 72,547, dated Feb. 23, 1983.

Primary Examiner—Elbert L. Roberts
Attorney, Agent, or Firm—Birch, Stewart, Kolasch & Birch

[57] ABSTRACT

A 6α-methylprednisolone derivative of the general formula:

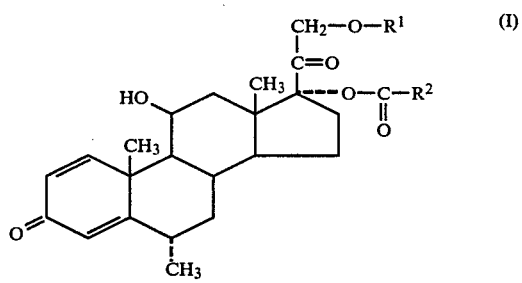

wherein $R^1$ is a hydrogen atom or stands for the grouping

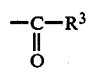

where $R^3$ is a straight or once-branched chain $C_{1-4}$ alkyl group, a phenyl group or a lower alkoxy- or alkylthio-methyl group, and $R^2$ is a straight or once-branched chain $C_{1-4}$ alkyl group, a phenyl group or a lower alkoxy- or alkylthio-methyl group, with the proviso that when $R^2$ is ethyl group, $R^1$ should not be a hydrogen atom or $R^3$ should not be ethyl group. This compound exhibits a strong local antiinflammatory effect and is, therefore, useful as a harmless external antiinflammatory drug for various dermal disorders and also as an antiallergic drug for treating asthma and the like allergic diseases.

12 Claims, No Drawings

6α-METHYLPREDNISOLONE DERIVATIVES

BACKGROUND AND FIELD OF THE INVENTION

The present invention relates to a new class of 6α-methylprednisolone derivatives, and more particularly to new 17α-acyloxy-21-hydroxy- or -acyloxy-11β-hydroxy-6α-methyl-1,4-pregnadiene-3,20-dione derivatives possessing useful pharmacological activities.

BACKGROUND OF THE INVENTION

In recent years, a number of corticosteroid compounds have been clinically employed for the purpose of exhibiting antirheumatic effect, antiinflammatory effect, antiallergic effect and antianaphylactic shock effect. Very recently, corticosteroid compounds have been used as locally effective external drugs rather than internal drugs in conjunction with the utility for antiinflammatory effect, so that various kinds of externally applicable corticosteroid drugs are now commercially available not only for clinical purposes but also for general use. A wide variety of corticosteroid compounds are already known which are derived from hydrocortisone, which is regarded as the fundamental compound of these corticosteroid compounds, by significantly modifying or redesigning the hydrocortisone structure in such manner that one or more hydroxy groups, methyl groups, halogen (bromine, chlorine and fluorine) atoms and/or double bonds are introduced into the skeleton structure of the fundamental compound or the originally existing hydroxy groups are esterified or acetonized. In the current situation, the majority of these steroid compounds contain a fluorine atom in the 9- or 6-position of the fundamental steroid structure. Such corticosteroid compounds are certainly excellent corticoid drugs possessing strong pharmacological effects but, on the other hand, involve a problem of safety in connection with the compounds to which the fluorine atom has been introduced, thus necessitating physicians' particular attention for clinical use of these compounds. When the metabolism and excretion of such compounds in vivo are taken into consideration, it can hardly be said, depending on administration term or dose, that no problem arises in respect of safety even if such compounds are used as external drugs. Although fluorine-containing corticosteroid compounds are still commercially available as potent antiinflammatory drugs, the use of the compounds themselves for clinical treatments is limited because of their harmful fluorine substituent. Accordingly, an attempt has also been made to develop a new class of corticosteroid compounds free of such harmful fluorine substituent while maintaining their useful pharmacological activities. Such attempt contemplates chemical modification of the fundamental compound, which, as so far reported, is acylation of the hydroxy group originally existing in the fundamental compounds. For example, Japanese Laid-open Patent Appln. No. Sho 56-86119 discloses 17α-propionyloxy-6α-methylprednisolone and 17α,21-dipropionyloxy-6α-methylprednisolone obtained by such modification. This procedure succeeded certainly in elimination of the harmful fluorine substituent from the steroid molecule, but the result of such modification revealed a failure in maintaining the expected pharmacological effects and very poor improvement in antiinflammatory effect. In the present status, therefore, no steroid compound has been reported or put into practical use as an externally applicable strong antiinflammatory drug. Thus, there is still a great demand in this art for developing further new class of steroid compounds free from any harmful substituent but enhanced in expected pharmacological activities to a practically acceptable level.

BRIEF SUMMARY OF THE INVENTION

Accordingly, it is an object of the present invention to provide a new class of 6α-methylprednisolone derivatives possessing a strong local antiinflammatory effect.

It is another object of the present invention to provide a new class of 17α-acyloxy-21-hydroxy- or -acyloxy-11β-hydroxy-6α-methyl-1,4-pregnadiene-3,20-dione derivatives useful especially as a harmless external antiinflammatory drug.

Other and further objects, features and advantages of the present invention will become apparent as the description proceeds.

DETAILED DESCRIPTION OF THE INVENTION

As a result of extensive researches made for developing a new class of corticosteroid compounds free of any harmful fluorine substituent which have a structure similar to the naturally occurring corticosteroid compounds and exhibit a strong antiinflammatory activity, it has now been found that new corticosteroid compounds derived from 6α-methylprednisolone by acylation of its 17α-hydroxy group or 17α,21-dihydroxy group with specific acyl reactants are devoid of a harmful fluorine substituent and exhibit a strong local antiinflammatory activity so as to utilize the compounds as external antiinflammatory drugs. The present invention has been accomplished on the basis of the above finding.

In accordance with the present invention, there are provided new 6α-methylprednisolone derivatives of the general formula:

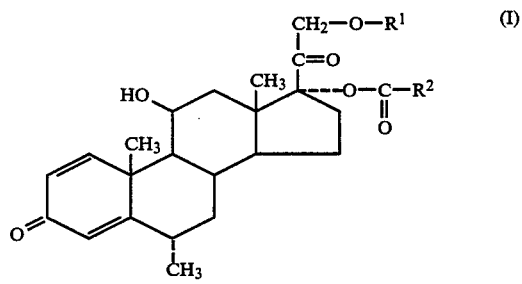

wherein $R^1$ is a hydrogen atom or stands for the grouping

where $R^3$ is a straight or once-branched chain $C_{1-4}$ alkyl group, a phenyl group or a lower alkoxy- or alkylthiomethyl group, and $R^2$ is a straight or once-branched chain $C_{1-4}$ alkyl group, a phenyl group or a lower alkoxy- or alkylthiomethyl group, with the proviso that when $R^2$ is ethyl group, $R^1$ should not be a hydrogen atom or $R^3$ should not be an ethyl group.

The 6α-methylprednisolone derivatives of the general formula (I) involve 17α-acyl compounds and 17α,21-diacyl compounds, depending on the definition of R¹. In the general formula (I), R² and R³ may be the same or different.

Illustrative of the straight or once-branched chain $C_{1-4}$ alkyl group are, for example, methyl, ethyl, n-propyl, isopropyl, n-butyl and isobutyl groups. The phenyl group is preferably the nucleus-unsubstituted phenyl group but may be a phenyl group substituted on the benzene ring with one or two lower alkyl groups. Examples of the lower alkoxy-methyl group include methoxymethyl, ethoxymethyl, n-propoxymethyl, isopropoxymethyl and n-butoxymethyl group, with the methoxymethyl being preferable. Examples of the lower alkylthio-methyl group include those corresponding to the above-mentioned alkoxymethyl groups, in which sulfur atom is substituted for the oxygen atom. A preferable example of the alkylthiomethyl group is methylthiomethyl group. The lower alkyl or alkoxy group is used herein to mean an alkyl or alkoxy group with 1–4 carbon atoms.

Accordingly, typical examples of the acyl group represented by the groupings

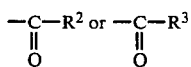

include acetyl, propionyl, n-butyryl, isobutyryl, n-valeryl, isovaleryl, benzoyl, p-methylbenzoyl, methoxyacetyl, ethoxyacetyl, methylthioacetyl and ethylthioacetyl groups. When R² is the same as R³, the two groupings

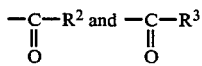

represent the same acyl group.

The 6α-methylprednisolone derivatives of the present invention represented by the general formula (I) are new compounds. Particularly preferable in the present invention are compounds represented by the general formulas:

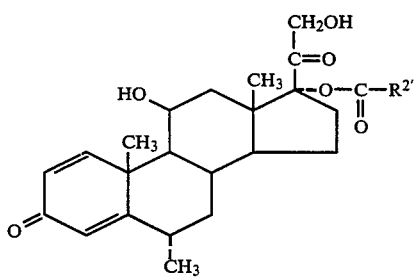

(II′)

and

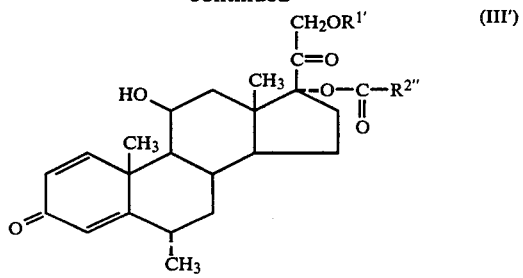

(III′)

In these formulas, $R^{2'}$ is a straight or once-branched chain $C_{3-4}$ alkyl group, a phenyl group or a lower alkoxy- or alkylthio-methyl group, $R^{1'}$ stands for the grouping

where R³ has the same meaning as given above, and $R^{2''}$ is a straight or once-branched chain $C_{1-4}$ alkyl group or a lower alkoxy- or alkylthio-methyl group. The present invention particularly relates to those 6α-methylprednisolone compounds of the general formula (I) wherein at least one of the substituents R¹ and R² has one of the above mentioned preferred meanings.

Prednisolone itself is a Δ¹-derivative of hydrocortisone and is reduced in mineral corticoid activity which is a side-effect of hydrocortisone. A prednisolone derivative obtained by introducing a methyl group into the 6α-position of prednisolone is called 6α-methylprednisolone which is 15–20% higher in the expected activity than the prednisolone itself and is an efficient drug exhibiting an outstanding activity against acute and chronic lymphoid leukemia. The compounds of the present invention are 6α-methylprednisolone derivatives carrying a specific acyl group or groups in their 17α-position or 17α,21-positions.

The new 6α-methylprednisolone derivatives of the present invention can be prepared according to various processes known per se. One of the preferable processes is comprised, for example, of the following steps:

6α-Methylprednisolone of the formula (IV):

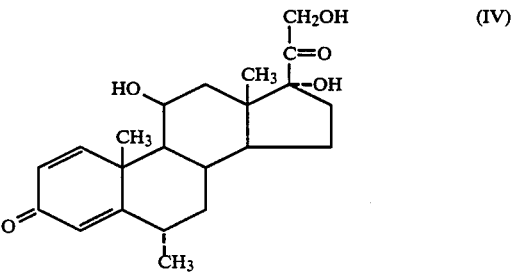

(IV)

is first reacted with an ortho ester of the general formula:

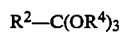 (V)

wherein R² has the same meanings as given above and R⁴ is a lower alkyl group, to form a cyclic 17α,21-ortho ester of 6α-methylprednisolone of the general formula:

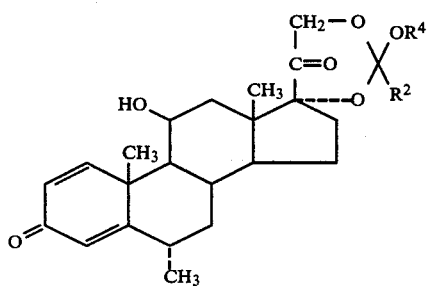

(VI)

wherein $R^2$ and $R^4$ have the same meanings as given above, and then this 17α,21-ortho ester is subjected to a ring-opening reaction to form a 17α-acyloxy-11β,21-dihydroxy-6α-methyl-1,4-pregnadiene-3,20-dione compound of the general formula:

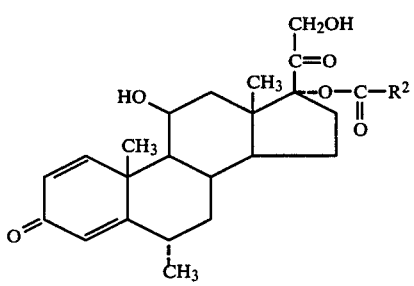

(II)

wherein $R^2$ has the same meanings as given above.

If a 17α,21-diacyloxy derivative is aimed at as the end product, the 17α-acyloxy-11β,21-dihydroxy compound of the general formula (II) obtained above is reacted with a compound of the general formula:

$R^3$—CO—X (VII)

wherein $R^3$ has the same meanings as given above and X is a hydroxyl group, a halogen atom or the grouping $R^3$—CO—O— where $R^3$ has the same meanings as given above, to form a compound of the general formula:

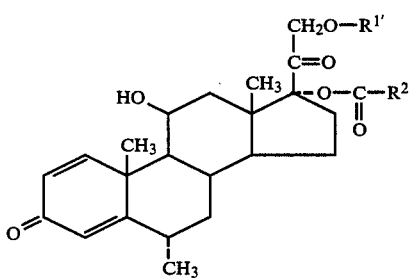

(III)

wherein $R^{1'}$ and $R^2$ have the same meanings as given above.

The ortho ester of the general formula(V) is suitably selected according to the acyl substituent $R^2$ to be introduced into 17α-hydroxy group of the starting 6α-methylprednisolone of the formula (IV). Usually, a methyl or ethyl group is selected as the lower alkyl group $R^4$ in view of easiness in preparation and availability of the ortho ester. Specifically, ethyl or methyl orthoacetate, orthopropionate, orthobutyrate, orthoisobutyrate, orthovalerate, orthoisovalerate, orthobenzoate, orthomethoxyacetate and orthomethylthioacetate can be utilized.

The compound of the general formula(VII) is also suitably selected according to the acyl substituent

to be introduced into 21-hydroxy group of the 17α-acyl-6α-methylprednisolone of the general formula (II) intermediately formed. This acylating compound is preferably used in the form of a functionally reactive derivative thereof, such as an acid halide or an acid anhydride in the presence of a base usually selected from a tertiary organic amine, e.g. triethylamine or pyridine.

In case the acylating compound of the formula (VII) is used as free acid (i.e. X=OH), the acylation is advantageously promoted by adding a dehydrating agent such as a carbodiimide, e.g. N,N'-dicyclohexylcarbodiimide, to the reaction system.

In detail, the cyclic 17α,21-ortho ester of 6α-methylprednisolone of the general formula (VI) is prepared generally by adding an ortho ester of the general formula (V) and a small amount of p-toluenesulfonic acid to a solution of 6α-methylprednisolone of the formula (IV) in a solvent and heating the mixture with stirring in an atmosphere of or under a current of an inert gas. Illustrative of the solvent for dissolving 6α-methylprednisolone are, for example, inert polar solvents such as dimethylformamide, diethylformamide, dimethylsulfoxide or dioxane. Nitrogen or argon is usually employed as the inert gas. The temperature usually adopted for heating the reaction mixture is within the range of from 60° C. to 120° C., preferably from 70° C. to 110° C., and the heating time is generally within the period of from 30 minutes to 15 hours, preferably from 1 hour to 8 hours. No special limitation exists in the proportion of the starting 6α-methylprednisolone to the ortho ester, but the latter is advantageously employed in molar excess. After the heating, the liquid reaction mixture is treated with a weak base and taken up in an ester or alkylene halide. As the weak base, a tertiary amine such as pyridine or triethylamine as well as a weak inorganic base such as sodium carbonate, potassium carbonate and potassium bicarbonate come into question. Addition of such weak base to the reaction mixture is effective to inhibit any decomposition of the resultant 17α,21-ortho ester (VI), thus serving to increase the yield of the product. Accordingly, this treatment is recommended or rather necessary in the preparation of the 17α,21-ortho esters. Preferable examples of the ester and alkylene halide to be mixed with the reaction mixture include ethyl acetate, methyl acetate, methylene chloride and ethylene chloride. The organic phase is then washed thoroughly with water, filtered to remove any solid impurities, dried with an inert dehydrating substance such as anhydrous sodium sulfate and concentrated under atmospheric or subatmospheric pressure. All of these treatments are conducted according to a conventional method usually adopted for after-treatments of the reaction products. The residue thus obtained is then crystallized from acetone-hexane. If it is difficult to crystallize out the product, the residue may be purified by the aid of column chromatography on silica gel impregnated with triethylamine. Usually, however, the crude product obtained as a crystalline or amorphous solid substance is used as such for the next step, i.e. the ring-opening reaction of the cyclic ortho ester.

The ring-opening reaction of the resultant cyclic 17α,21-ortho ester of the general formula (VI) is carried out by the aid of an acid normally in the presence of a suitable solvent, for example, a lower alkanol such as methanol. This reaction proceeds very smoothly, but usually with the formation of the 17α-acylated compound aimed at together with a small amount of the corresponding 21-acylated compound as by-product. It is therefore recommended to adjust the acidic condition employed to a pH range of 2–4 in order to obtain the desired 17α-acylated compound selectively. Such pH range can be made up usually by addition of an organic acid such as oxalic acid or citric acid to the reaction system. Alternatively, a buffered solution having a pH value of 3–4 can be used to achieve a favorable result. It has now been found surprisingly by the present inventors that the use of a small amount of iodine ($I_2$) for the ring-opening reaction of the cyclic ortho ester serves to increase the yield of the 17α-acylated compound aimed at. The reaction mixture thus obtained generally contains the desired 17α-acylated compound and a small amount of the contaminating 21-acylated compound. A column chromatography technique using silica gel is usually employed to eliminate the contaminant thereby obtaining the desired 17α-acylated compound in a purer form. Alternatively, a preparative thin layer chromatography technique using silica gel may also be utilized for this purpose.

In case 17α, 21-diacylated 6α-methylprednisolone compounds of the general formula (III) are to be prepared as end products, the 21-hydroxy group of the 17α-acylated compounds thus obtained is acylated according to the method known per se with an acylating compound of the general formula (VII). This acylation is advantageously carried out by using the compound of the general formula (II) and a compound of the general formula (VII) wherein X is a halogen atom or the grouping $R^3$—CO—O— in the presence of a tertiary amine such as triethylamine or pyridine. This acylation is promoted very smoothly under a mild condition. In case the acylating compound in the form of an acid anhydride is used, the acylation will be completed usually at ambient or room temperature within the period from 1 to 40 hours, preferably 2–30 hours. It is possible to warm the reaction mixture slightly to accelerate the reaction thereby shortening the reaction time. In case the acylating compound in the form of an acid halide (chloride or bromide) is used, the acylation could be carried out under a milder condition, for example, at 0° C. for 20–40 minutes. The above acylation is normally carried out in the presence of an excess amount of a tertiary amine in an inert solvent such as methylene chloride. It is preferable to employ the acylating agent in a slightly excess stoichiometrical amount against the 17α-acyl compound of the general formula (II). If the acylating compound remains unreacted in the reaction mixture, it can easily be decomposed by addition of a lower alkanol to the reaction mixture. After completion of the reaction, the reaction mixture can be treated according to the conventional method, for example, by diluting the reaction mixture with a suitable solvent such as ethyl acetate, washing the organic phase with water sufficiently, filtering the organic phase to remove any solid impurities and concentrated usually under reduced pressure. The crude 17α,21-diacylated product thus obtained can be purified in the method known per se by recrystallization, for example, from acetone-hexane or by means of a column chromatography technique or a preparative thin layer chromatography technique using silica gel. It is also possible to subject a residue obtained by concentrating the reaction mixture directly to such chromatographic treatment for purification.

The new 6α-methylprednisolone derivatives obtained by the above one- or two-step acylation were identified to be 17α-acyloxy-11β, 21-dhydroxy-6α-methyl-1,4-pregnadiene-3,20-dione compounds or 17α, 21-diacyloxy-11β-hydroxy-6α-methyl-1,4-pregnadiene-3,20-dione compounds by subjecting the derivatives to analyses including the measurements of infra-red absorption spectra (IR), nuclear magnetic resonance spectra (NMR), mass spectra (MS) and elementary analysis.

The new 6α-methylprednisolone derivatives of the present invention represented by the general formula (I) exhibit a strong local antiinflammatory activity and thus can be utilized clinically for chemotherapy of various dermal disorders, for example, acute or chronic eczema, contact dermatitis, eczema seborrhoicorum, atopic dermatitis, eczema infantum and psoriasis vulgaris. The new compounds of the present invention can also be utilized for treating asthma and other various allergic diseases. For the therapy of these diseases, the 6α-methylprednisolone derivatives can be used in various types of pharmaceutical preparations, for example, ointments, creams, lotions, liquid paints, plasters and powders.

The antiinflammatory activity exhibited by the new 6α-methylprednisolone derivatives is extremely outstanding and this fact can be proved by evaluating the activity according to the vasoconstriction test. Given below are the testing method for evaluation of the pharmacological activity and results thereof.

Testing method

From the compounds of the present invention represented by the general formula (I) and compounds for comparative tests (controls), ointments containing these compounds each in a concentration of 0.01% were prepared. These ointments were randomly applied in a definite amount (about 20 mg) by a controller having no concern with the evaluation of activity onto a plastic bandage for patch test (Finn Chamber; Epitest Ltd. Oy, Finland) to prepare test pieces. Each of these test pieces was applied onto the skin in the flexor aspects of both forearms of 10 healthy adult males. After the lapse of 16 hours, all the test pieces of the plastic bandage were peeled off and the compounds remaining on the skin were gently washed out with a soap solution.

Evaluation

The vasoconstrictive activity in terms of balancing degree on the skin after 2 hours and 6 hours were determined by 2 judging persons using the following four degrees:
 + +(marked)
 +(medium)
 ±(slight)
 −(inactive)
according to the blanching degree. The numerals 3, 2, 1 and 0 were arbitarily given to the above four degrees, respectively, and the numerical data on the 10 volunteers were summed up (30.0 in the maximum value). The vasoconstrictive activity was calculated as a mean value of the results obtained by the 2 judging persons.
Tables 1 and 2 show the results of this test.

TABLE 1

| No. | Compound | Concentration[a] (w/w %) | Vasoconstrictive Activity[b] after 2 Hrs. | after 6 Hrs. |
|---|---|---|---|---|
| 1 | 17α-butyryloxy-11β,21-dihydroxy-6α-methyl-1,4-pregnadiene-3,20-dione | | 29.0 | 25.5 |
| 2 | 11β,21-dihydroxy-17α-isobutyryloxy-6α-methyl-1,4-pregnadiene-3,20-dione | | 29.0 | 26.0 |
| 3 | 11β,21-dihydroxy-6α-methyl-17α-valeryloxy-1,4-pregnadiene-3,20-dione | | 21.5 | 18.5 |
| 4 | 11β,21-dihydroxy-17α-isovaleryloxy-6α-methyl-1,4-pregnadiene-3,20-dione | | 27.5 | 22.5 |
| 5 | 17α-benzoyloxy-11β,21-dihydroxy-6α-methyl-1,4-pregnadiene-3,20-dione | | 26.5 | 23.5 |
| 6 | 17α,21-diacetoxy-11β-hydroxy-6α-methyl-1,4-pregnadiene-3,20-dione | | 22.5 | 11.0 |
| 7 | 21-acetoxy-11β-hydroxy-6α-methyl-17α-propionyloxy-1,4-pregnadiene-3,20-dione | | 28.0 | 16.0 |
| 8 | 17α-acetoxy-21-benzoyloxy-11β-hydroxy-6α-methyl-1,4-pregnadiene-3,20-dione | | 22.5 | 12.0 |
| 9 | 17α-acetoxy-11β-hydroxy-6α-methyl-21-propionyloxy-1,4-pregnadiene-3,20-dione | | 23.0 | 14.5 |
| 10 | 21-butyryloxy-11β-hydroxy-6α-methyl-17α-propionyloxy-1,4-pregnadiene-3,20-dione | | 25.5 | 13.0 |
| 11 | 11β-hydroxy-21-isobutyryloxy-6α-methyl-17α-propionyloxy-1,4-pregnadiene-3,20-dione | | 24.0 | 13.5 |
| 12 | 21-benzoyloxy-11β-hydroxy-6α-methyl-17α-propionyloxy-1,4-pregnadiene-3,20-dione | | 24.5 | 18.5 |
| 13 | 21-acetoxy-17α-butyryloxy-11β-hydroxy-6α-methyl-1,4-pregnadiene-3,20-dione | | 26.0 | 18.5 |
| 14 | 17α-butyryloxy-11β-hydroxy-6α-methyl-21-propionyloxy-1,4-pregnadiene-3,20-dione | | 28.5 | 24.0 |
| 15 | 17α,21-dibutyryloxy-11β-hydroxy-6α-methyl-1,4-pregnadiene-3,20-dione | | 26.0 | 24.0 |
| 16 | 21-acetoxy-11β-hydroxy-17α-isobutyryloxy-6α-methyl-1,4-pregnadiene-3,20-dione | | 28.5 | 15.5 |
| 17 | 17α-butyryloxy-11β-hydroxy-21-isobutyryloxy-6α-methyl-1,4-pregnadiene-3,20-dione | | 25.0 | 13.0 |
| 18 | 11β-hydroxy-17α-isobutyryloxy-6α-methyl-21-propionyloxy-1,4-pregnadiene-3,20-dione | | 22.5 | 15.5 |
| 19 | 11β-hydroxy-17α,21-diisobutyryloxy-6α-methyl-1,4-pregnadiene-3,20-dione | | 17.0 | 13.0 |
| 20 | 21-acetoxy-11β-hydroxy-6α-methyl-17α-valeryloxy-1,4-pregnadiene-3,20-dione | | 22.0 | 14.5 |
| 21 | 21-butyryloxy-11β-hydroxy-17α-isobutyryloxy-6α-methyl-1,4-pregnadiene-3,20-dione | | 21.0 | 15.5 |
| 22 | 11β-hydroxy-17α-isovaleryloxy-6α-methyl-21-propionyloxy-1,4-pregnadiene-3,20-dione | | 18.5 | 17.0 |
| 23 | 11β-hydroxy-6α-methyl-21-propionyloxy-17α-valeryloxy-1,4-pregnadiene-3,20-dione | | 19.5 | 15.0 |
| 24 | 21-acetoxy-11β-hydroxy-17α-isovaleryloxy-6α-methyl-1,4-pregnadiene-3,20-dione | | 24.0 | 19.0 |
| | Controls | | | |
| | hydrocortisone 21-acetate | 1.0 | 6.0 | 2.5 |
| | 6α-methylprednisolone | 0.01 | 6.0 | 4.5 |
| | betamethasone 17-valerate | 0.01 | 25.0 | 22.0 |
| | ointment base | — | 3.0 | 2.0 |
| | non-treated | — | 1.5 | 1.0 |

[a]Each concentration of the Compounds Nos. 1–24 is 0.01%.
[b]Activity is expressed by a score for blanching degree, which correlates well to antiinflammatory activity (maximum is 30.0).

TABLE 2

| No. | Compound | Concentration[a] (w/w %) | Vasoconstrictive activity[b] after 2 Hrs. | after 6 Hrs. |
|---|---|---|---|---|
| 1 | 17α-butyryloxy-11β-hydroxy-6α-methyl-21-methylthioacetoxy-1,4-pregnadiene-3,20-dione | | 14.5 | 10.5 |
| 2 | 11β-hydroxy-17α-methoxyacetoxy-6α-methyl-21-propionyloxy-1,4-pregnadiene-3,20-dione | | 16.0 | 8.0 |
| 3 | 21-butyryloxy-11β-hydroxy-17α-methoxyacetoxy-6α-methyl-1,4-pregnadiene-3,20-dione | | 17.5 | 12.0 |
| 4 | 11β,21-dihydroxy-6α-methyl-17α-methylthioacetoxy-1,4-pregnadiene-3,20-dione | | 12.5 | 8.0 |
| 5 | 11β-hydroxy-6α-methyl-17α-methylthioacetoxy-21-propionyloxy-1,4-pregnadiene-3,20-dione | | 23.0 | 18.5 |
| 6 | 21-butyryloxy-11β-hydroxy-6α-methyl-17α-methylthioacetoxy-1,4-pregnadiene-3,20-dione | | 18.5 | 14.0 |
| 7 | 11β-hydroxy-21-methoxyacetoxy-6α-methyl-17α-methylthioacetoxy-1,4-pregnadiene-3,20-dione | | 14.5 | 12.0 |

TABLE 2-continued

| No. | Compound | Concentration[a] (w/w %) | Vasoconstrictive activity[b] after 2 Hrs. | after 6 Hrs. |
|-----|----------|--------------------------|-------------------------------------------|--------------|
| 8 | 17α-butyryloxy-11β-hydroxy-21-methoxyacetoxy-6α-methyl-1,4-pregnadiene-3,20-dione | | (27.0) | (21.0) |
| | Controls | | | |
| | Hydrocortisone 21-acetate | 1.0 | 4.5(6.0) | 2.5(2.5) |
| | 6α-Methylprednisolone | 0.01 | 4.0(6.0) | 3.5(4.5) |
| | Betamethasone 17-valerate | 0.01 | 17.0(25.0) | 16.5(22.0) |

[a]Each concentration of the Compounds Nos. 1-8 is 0.01%.
[b]Activity is expressed by a score for blanching degree which correlates well to antiinflammatory activity (maximum is 30.0). The scores showed in the parentheses of controls are employed for that of the Compound No. 8.

As is evident from the results shown in Tables 1 and 2, the compounds of the present invention are extremely strong in vasoconstrictive activity in comparison with the starting 6α-methylprednisolone. Some of the compounds of the present invention are much more effective in the activity than commercially available betamethasone 17-valerate.

The present invention will now be explained in more detail by way of examples wherein the new compounds of the present invention and preparation thereof are illustrated.

EXAMPLE 1

17α-Butyryloxy-11β,21-dihydroxy-6α-methyl-1,4-pregnadiene-3,20-dione (a) In 6 ml of dimethylformamide was dissolved 374 mg of 6α-methylprednisolone. To this solution were added 380 mg of ethyl orthobutyrate and then 9 mg of p-toluenesulfonic acid. The mixture was heated at 80° C. with stirring for 1.5 hours in a stream of argon and the reaction liquid was poured into 50 ml of ethyl acetate. To the liquid mixture were added immediately 1 ml of a 10% solution of sodium carbonate and 30 ml of water. The mixture was well shaken and the ethyl acetate phase was separated, washed twice with 30 ml of water and dried over anhydrous sodium sulfate. The solution was then filtered and the filtrate was evaporated to obtain a crude crystalline substance which was recrystallized from acetone-hexane whereby 430 mg (yield: 90.9%) of 6α-methylprednisolone 17α,21-ethyl orthobutyrate was obtained as colorless needle crystals.

M.P. 164.0°-166.0° C. (with decomp.).
IR $\nu_{max}^{KBr}$ cm$^{-1}$: 3340, 1720, 1645.
MS m/e: 473 (M$^+$+1), 472 (M$^+$), 427, 356, 311, 297, 279, 161, 136, 135 (base peak), 121.
Elementary analysis (as $C_{28}H_{40}O_6$): Calc. (%): C 71.16; H 8.53. Found (%): C 71.03; H 8.71.

In 8 ml of methanol was dissolved 400 mg of 6α-methylprednisolone 17α,21-ethyl orthobutyrate. To this solution was added 1 ml of 2N-oxalic acid, and the mixture was warmed for 30 minutes at 40°-45° C. The solvent was removed by distillation under reduced pressure and 80 ml of ethyl acetate was added to the residue. The ethyl acetate solution was washed twice with 30 ml of water, dried over anhydrous sodium sulfate and evaporated under subatmospheric pressure to obtain a crude product, which was subjected to column chromatography on silica gel and fractionated with methylene chloride for purification whereby 302 mg (yield: 80.2%) of 17α-butyryloxy-11β,21-dihydroxy-6α-methyl-1,4-pregnadiene-3,20-dione was obtained.

This compound was colorless and amorphous but was confirmed to be pure in view of its physical properties and as the results of various analyses shown hereunder.

TLC (silica gel): Rf 0.51 (single spot, benzene:ethanol=5:1).
IR $\nu_{max}^{KBr}$ cm$^{-1}$: 3400, 1720, 1710, 1650.
NMR δCDCl$_3$: 0.80-1.20 (9H, m, —CH$_2$CH$_3$, C$_{18}$—CH$_3$ and C$_{6α}$—CH$_3$), 1.47 (3H, s, C$_{19}$—CH$_3$), 4.26 (2H, br.s, C$_{21}$—CH$_2$), 4.52 (1H, br, C$_{11}$—CH), 6.03 (1H, s, C$_4$—CH), 6.28 (1H, d, J=10 Hz, C$_2$—CH), 7.36 (1H, d, J=10 Hz, C$_1$—CH).
MS m/e: 445 (M$^+$+1), 444 (M$^+$), 413 (M$^+$−31), 356, 327, 309, 297, 279, 161, 136 (base peak), 135, 121.
Elementary analysis (as $C_{26}H_{36}O_6$): Calc. (%): H 70.24; H 8.16. Found (%): H 70.12; H 8.29.

(b) In 2 ml of dimethylformamide was dissolved 200 mg of 6α-methylprednisolone. To this solution were added 180 mg of methyl orthobutyrate and 8 mg of p-toluenesulfonic acid. The mixture was heated at 110° C. under a nitrogen current with stirring for one hour. To the reaction liquid were added at room temperature 1 ml of pyridine and 50 ml of ethyl acetate, and the mixture was weashed twice with 30 ml of water. The ethyl acetate phase was dried over anhydrous sodium sulfate and filtered. The filtrate was concentrated to obtain a crude product which was then recrystallized from acetone-hexane whereby 175 mg (yield: 71.3%) of 6α-methylprednisolone 17α,21-methyl orthobutyrate was obtained.

Next, 100 mg of this compound was dissolved in 6 ml of methanol and 0.5 ml of a buffered solution of sodium acetate was added. The mixture was stirred overnight at room temperature and the reaction liquid was treated in the same manner as described in the foregoing (a) to obtain a crude product which was subjected to preparative thin layer chromatography on silica gel for purification whereby 71 mg (yield: 72.8%) of 17α-butyryloxy-11β,21-dihydroxy-6α-methyl-1,4-pregnadiene-3,20-dione was obtained. This compound was in agreement in physical properties and analytical data with that obtained in the above (a).

EXAMPLE 2

11β,21-Dihydroxy-17α-isobutyryloxy-6α-methyl-1,4-pregnadiene-3,20-dione (a) In 6 ml of dimethylformamide was dissolved 750 mg of 6α-methylprednisolone. To this solution were added 890 mg of methyl orthobutyrate and then 34 mg of p-toluenesulfonic acid. The mixture was heated at 80° C. with stirring in a stream of argon for one hour and then 80 ml of ethyl acetate was poured into the reaction liquid. Then, 2 ml of a 10% solution of sodium carbonate was immediately added to the reaction liquid, and 50 ml of water was added thereto. The liquid mixture was well shaken and the ethyl acetate layer was separated, washed with water and dried over anhydrous sodium sulfate. The ethyl acetate was distilled off and the resultant crude crystalline product was recrystallized whereby 862 mg (yield: 93.9%) of 6α-methylprednisolone 17α,21-methyl orthoisobutyrate was obtained as colorless needle crystals (m.p. 172.0°-175.0° C. with decomp.).

Analytical data of this compound were as follows:
IR $\nu_{max}^{KBr}$ cm$^{-1}$: 3320 (OH), 1715 (C=O), 1645 (C=O).

MS m/e: 459 (M$^+$+1), 458 (M$^+$), 427 (M$^+$−31), 325, 297, 279, 161, 136 (base peak), 135, 121.

Elementary analysis (as $C_{27}H_{38}O_6$): Calc. (%): C 70.71; H 8.35. Found (%): C 70.58; H 8.41.

In 20 ml of methanol was dissolved 460 mg of the thus obtained 6α-methylprednisolone 17α,21-methyl orthoisobutyrate. To this solution was added 1 ml of 2N-oxalic acid, and the mixture was warmed at 40°-50° C. for 10 minutes. The solvent was distilled off under reduced pressure and 50 ml of ethyl acetate was added to the residue. The ethyl acetate solution was washed with water and dried over anhydrous sodium sulfate, and the solvent was removed by distillation under reduced pressure to obtain a crystalline residue which was then subjected to column chromatography on silica gel, eluted and fractionated with methylene chloride whereby 344 mg (yield: 77.3%) of 11β,21-dihydroxy-17α-isobutyryloxy-6α-methyl-1,4-pregnadiene-3,20-dione was obtained. This compound was a colorless amorphous substance but was confirmed to be pure in view of the following physical properties and spectra:

TLC (silica gel): Rf 0.52 (single spot, benzene:ethanol=4:1).

IR $\nu_{max}^{KBr}$ cm$^{-1}$: 3400 (OH), 1720 (C=O), 1710 (C=O), 1650 (C=O).

NMRδCDCl$_3$: 0.95 (3H, s, C$_{18}$—CH$_3$), 1.15 (6H, d,

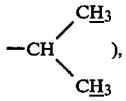

1.15 (3H, d, C$_{6α}$—CH$_3$), 1.47 (3H, s, C$_{19}$—CH$_3$), 4.23 (2H, s, C$_{21}$—CH$_2$), 4.50 (1H, br, C$_{11}$—CH), 6.05 (1H, s, C$_4$—CH), 6.28 (1H, d, J=10 Hz, C$_2$—CH), 7.30 (1H, d, J=10 Hz, C$_1$—CH).

MS m/e: 445 (M$^+$+1), 444 (M$^+$), 413 (M$^+$−31), 358, 297, 279, 161, 136, 135 (base peak), 121.

Elementary analysis (as $C_{26}H_{36}O_6$): Calc. (%): C 70.24; H 8.16. Found (%): C 70.28; H 8.31.

(b) To 3 ml of methylene chloride was added 100 mg of 6α-methylprednisolone 17α,21-methyl orthoisobutyrate obtained in the foregoing (a). To this mixture was added under agitation 5 mg of iodine, and the reaction was allowed to proceed at room temperature for 30 minutes. The reaction liquid was then concentrated under reduced pressure and the resultant crude product was subjected to preparative thin layer chromatography (silica gel) whereby 82 mg of 11β,21-dihydroxy-17α-isobutyryloxy-6α-methyl-1,4-pregnadiene-3,20-dione was obtained. This compound was in agreement in physical properties and spectrum data in IR, NMR and MS with the title compound obtained in the preceding (a).

EXAMPLE 3

11β,21-Dihydroxy-6α-methyl-17α-valeryloxy-1,4-pregnadiene-3,20-dione

In 3 ml of dimethylformamide was dissolved 374 mg of 6α-methylprednisolone. To this solution were added 324 mg of methyl orthovalerate and then 17 mg of p-toluenesulfonic acid. The mixture was heated at 90° C. with stirring under an argon current for 5 hours. To the reaction liquid were then added at room temperature 50 ml of ethyl acetate and 0.5 ml of a 10% aqueous solution of sodium carbonate. To this mixture was further added 30 ml of water, and the whole was well shaken. The ethyl acetate layer was separated, washed twice with 30 ml of water and then dried over anhydrous sodium sulfate. The ethyl acetate solution was filtered and the filtrate was concentrated to obtain a crude product which was then subjected to a separation treatment using column chromatography on silica gel impregnated with triethylamine whereby 433 mg (yield: 91.7%) of 6α-methylprednisolone 17α,21-methyl orthovalerate was obtained as a colorless amorphous solid. Shown below are various analytical data of this compound.

IR $\nu_{max}^{KBr}$ cm$^{-1}$: 3400 (OH), 1720 (C=O), 1645 (C=O).

MS m/e: 473 (M$^+$+1), 472 (M$^+$), 441, 356, 297, 279, 161, 136, 135 (base peak), 121, 85.

Elementary analysis (as $C_{28}H_{40}O_6$): Calc. (%): C 71.16; H 8.53. Found (%): C 71.23; H 8.69.

In 8 ml of methanol was dissolved 236 mg of the 6α-methylprednisolone 17α,21-methyl orthovalerate thus obtained, and the solution was warmed at 40° C. To the solution was added 0.5 ml of 2N-oxalic acid, and the mixture was warmed with stirring for 10 minutes. The solvent was then distilled off under reduced pressure and the resultant residue was subjected to preparative thin layer chromatography whereby 187 mg (yield: 81.7%) of 11β,21-dihydroxy-6α-methyl-17α-valeryloxy-1,4-pregnadiene-3,20-dione was obtained as a colorless amorphous solid. The structure of this compound was confirmed by the following physical properties and results of various analyses:

TLC: Rf 0.53 (silica gel, single spot, benzene:ethanol=4:1).

IR $\nu_{max}^{KBr}$ cm$^{-1}$: 3400 (OH), 1720 (C=O), 1715 (C=O), 1655 (C=O).

NMRδppm (CDCl$_3$): 0.95 (3H, s, C$_{18}$—CH$_3$), 0.88-1.25 (3H, m, CH$_2$CH$_2$CH$_2$CH$_3$), 1.11 (3H, d, J=6 Hz, C$_{6α}$—CH$_3$), 1.52 (3H, s, C$_{19}$—CH$_3$), 4.28 (2H, s, C$_{21}$—CH$_2$), 4.52 (1H, br, C$_{11}$—CH), 6.02 (1H, br.s, C$_4$—CH), 6.24 (1H, d, J=10 Hz, C$_2$—CH), 7.38 (1H, d, J=10 Hz, C$_1$—CH).

MS m/e: 459 (M$^+$+1), 458 (M$^+$), 441, 440, 427, 356, 327, 325, 297, 281, 279, 161, 136 (base peak), 135, 121, 85.

Elementary analysis (as $C_{27}H_{38}O_6$): Calc. (%): C 70.72; H 8.35. Found (%): C 70.59; H 8.53.

EXAMPLE 4

11β,21-Dihydroxy-17α-isovaleryloxy-6α-methyl-1,4-pregnadiene-3,20-dione

In 6 ml of dimethylformamide was dissolved 749 mg of 6α-methylprednisolone. To this solution were added 973 mg of methyl orthoisovalerate and 34 mg of p-toluenesulfonic acid, and the mixture was heated at 80° C. with stirring under an argon current for one hour. To the reaction liquid were then added at room temperature 80 ml of ethyl acetate, 0.5 ml of a 10% solution of sodium carbonate and 30 ml of water, and the mixture was well shaken. The ethyl acetate layer was separated, washed twice with 30 ml of water and dried over anhydrous sodium sulfate. The ethyl acetate solution was filtered and the filtrate was concentrated to obtain a crude product which was then recrystallized from benzene-hexane whereby 783 mg (yield: 82.8%) of 6α-methylprednisolone 17α,21-methyl orthoisovalerate was obtained as colorless needle crystals.

M.P. 168.0°–171.0° C. (with decomp.).

IR $\nu_{max}^{KBr}$ cm$^{-1}$: 3400, 1715, 1650.

MS m/e: 473 (M$^+$+1), 472 (M$^+$), 441 (M$^+$−31), 356, 297, 161, 136, 135 (base peak), 121.

Elementary analysis (as $C_{28}H_{40}O_6$): Calc. (%): C 71.16; H 8.53. Found (%): C 71.01; H 8.41. In 20 ml of methanol was dissolved 720 mg of 6α-methylprednisolone 17α,21-methyl orthoisovalerate. To the solution was added 2 ml of 2N-oxalic acid, and the mixture was warmed at 40° C. for 15 minutes. The solvent was then distilled off and 80 ml of ethyl acetate was added to the residue. The ethyl acetate phase was washed with 1 ml of a 10% solution of sodium carbonate and 30 ml of water, dried over anhydrous sodium sulfate and concentrated to obtain a crude product which was then subjected to column chromatography on silica gel whereby 486 mg (yield: 69.5%) of 11β,21-dihydroxy-17α-isovaleryloxy-6α-methyl-1,4-pregnadiene-3,20-dione was obtained. This compound was colorless and amorphous but was confirmed to be pure in view of the its physical properties and various analytical data shown below.

TLC (silica gel): Rf 0.53 (single spot, benzene:ethanol=4:1).

IR $\nu_{max}^{KBr}$ cm$^{-1}$: 3400, 1720, 1710, 1650.

NMRδCDCl$_3$: 0.90 (3H, s, C$_{18}$—CH$_3$), 0.96 (6H, s,

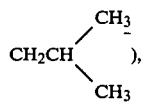

1.11 (3H, d, J=6 Hz, C$_{6\alpha}$—CH$_3$), 1.97 (3H, s, C$_{19}$—CH$_3$), 4.30 (2H, s, C$_{21}$—CH$_2$), 4.50 (1H, br, C$_{11}$—CH), 6.02 (1H, s, C$_4$—CH), 6.27 (1H, d, J=10 Hz, C$_2$—CH), 7.32 (1H, d, J=10 Hz, C$_1$—CH).

MS m/e: 459 (M$^+$+1), 458 (M$^+$), 440 (M$^+$−18), 427 (M$^+$−31), 356, 338, 327, 325, 281, 161, 136 (base peak), 135, 121.

Elementary analysis (as $C_{27}H_{38}O_6$): Calc. (%): C 70.71 H 8.35. Found (%): C 70.62 H 8.57.

EXAMPLE 5

17α-benzoyloxy-11β,21-dihydroxy-6α-methyl-1,4-pregnadiene-3,20-dione

A mixture of 2.0 g of 6α-methylprednisolone, 2.0 g of methyl orthobenzoate, 8 ml of dimethylformamide and 0.09 g of p-toluenesulfonic acid was heated at 80° C. with stirring under an argon current for 5 hours. To this reaction liquid were then added at room temperature 4 ml of a 10% aqueous solution of sodium carbonate, 40 ml of water and 100 ml of ethyl acetate, and the mixture was shaken. The ethyl acetate layer was separated, washed with water, dried over anhydrous sodium carbonate and filtered. The filtrate was concentrated under reduced pressure and the resultant crude product was subjected to column chromatography on silica gel impregnated with triethylamine and eluted with methylene chloride whereby 1.75 g (yield: 66.4%) of 6α-methylprednisolone 17α,21-methyl orthobenzoate was obtained, which showed a single spot in TLC (silica gel).

Although this compound was a colorless amorphous substance, it was identified by the following IR-absorption and mass spectral data and the result of elementary analysis:

IR $\nu_{max}^{KBr}$ cm$^{-1}$: 3350 (OH), 1715 (C=O), 1645 (C=O).

MS m/e: 493 (M$^+$+1), 492 (M$^+$), 475, 461 (M$^+$−31), 356, 297, 279, 161, 136, 135, 105 (base peak), 77.

Elementary analysis (as $C_{30}H_{36}O_6$): Calc. (%): C 73.14; H 7.37. Found (%): C 73.02; H 7.49.

In 30 ml of methanol was dissolved 1.5 g of the 6α-methylprednisolone 17α,21-methyl orthobenzoate thus obtained. To this solution was added 15 ml of a sodium acetate buffered solution, and the mixture was warmed at 40° C. for 10 minutes. The solvent was distilled off under reduced pressure and the resulting residue was subjected to preparative thin layer chromatography (silica gel) whereby 1.17 g (yield: 80.8%) of 17α-benzoyloxy-11β,21-dihydroxy-6α-methyl-1,4-pregnadiene-3,20-dione was obtained as a colorless amorphous substance. The physical properties and spectral data of this compounds are as follows:

TLC (silica gel): Rf 0.53 (single spot, benzene:ethanol=4:1).

IR $\nu_{max}^{KBr}$ cm$^{-1}$: 3400 (OH), 1710 (C=O), 1705 (C=O), 1650 (C=O).

NMRδCDCl$_3$: 1.04 (3H, s, C$_{18}$—CH$_3$), 1.14 (3H, d, C$_{6\alpha}$—CH$_3$), 1.48 (3H, s, C$_{19}$—CH$_3$), 4.32 (2H, s, C$_{21}$—CH$_2$), 4.57 (1H, br, C$_{11}$—CH), 6.06 (1H, s, C$_4$—CH), 6.30 (1H, d, J=10 Hz, C$_2$—CH), 7.35 (1H, d, J=10 Hz, C$_1$—CH), 7.40–8.10 (5H, m, Ph).

MS m/e: 479 (M$^+$+1), 478 (M$^+$), 447 (M$^+$−31), 327, 309, 297, 281, 161, 136, 135, 122, 105 (base peak), 77.

Elementary analysis (as $C_{29}H_{34}O_6$): Calc. (%): C 72.78; H 7.16. Found (%): C 72.89; H 7.33.

EXAMPLE 6

17α,21-diacetoxy-11β-hydroxy-6α-methyl-1,4-pregnadiene-3,20-dione

To 3 ml of dimethylformamide was dissolved 749 mg of 6α-methylprednisolone. To this solution were added 649 mg of ethyl orthoacetate and 17 mg of p-toluenesulfonic acid, and the mixture was heated at 75° C. with stirring for 1.5 hours. To the reaction liquid were then added at room temperature successively 80 ml of ethyl acetate, 0.5 ml of a 10% solution of sodium carbonate and 30 ml of water, and the mixture was shaken. The ethyl acetate layer was separated, washed twice with 30 ml of water, dried over anhydrous sodium sulfate and filtered. The filtrate was concentrated to obtain a crude product as a crystalline solid, which was recrystallized from acetone-hexane whereby 822 mg (yield: 92.5%) of 6α-methylprednisolone 17α,21-ethyl orthoacetate was obtained as colorless needle crystals.

M.P. 134.0°–136.0° C. (with decomp.).

IR $\nu_{max}^{KBr}$ cm$^{-1}$: 3440, 1715, 1650.

MS m/e: 445 (M$^+$+1), 444 (M$^+$), 399, 356, 297, 279, 237, 161, 136, 135 (base peak), 121.

Elementary analysis (as $C_{26}H_{36}O_6$): Calc. (%): C 70.24; H 8.16. Found (%): C 70.13; H 8.08.

In 8 ml of methanol was dissolved 270 mg of 6α-methylprednisolone 17α,21-ethyl orthoacetate. To this solution was added 1.5 ml of 2N-oxalic acid, and the mixture was heated at 40° C. for 10 minutes. The reaction liquid was concentrated and the resultant residue was well shaken with 50 ml of ethyl acetate, 1 ml of a 10% solution of sodium carbonate and 30 ml of water. The ethyl acetate layer was separated, washed twice with 30 ml of water, dried over anhydrous sodium sulfate and filtered. The filtrate was concentrated to obtain a crude product which was then subjected to preparative thin layer chromatography on silica gel whereby 177 mg (yield: 69.8%) of 17α-acetoxy-11β,21-dihydroxy-6α-methyl-1,4-pregnadiene-3,20-dione was obtained.

In 3 ml of methylene chloride was dissolved 114 mg of the thus obtained 17α-acetyl compound. To this solution were added 56 mg of acetic anhydride and 101 mg of triethylamine and the mixture was stirred at room temperature for 8 hours. To the solution was added 1 ml of dry methanol, and the mixture was allowed to stand overnight and concentrated under reduced pressure. The resultant residue was purified by subjecting it directly to preparative thin layer chromatography (silica gel) and then recrystallized from acetone-hexane whereby 105 mg (yield: 83.3%) of 17α,21-diacetoxy-11β-hydroxy-6α-methyl-1,4-pregnadiene-3,20-dione was obtained as colorless fine needle crystals. Below are physical properties and various analytical data of this compound.

M.P. 221.0°–224.0° C.

TLC (silica gel): Rf 0.37 (single spot, benzene:ethanol=10:1).

IR $\nu_{max}^{KBr}$ cm$^{-1}$: 3380, 1755, 1730, 1650.

NMRδCDCl$_3$: 1.03 (3H, s, C$_{18}$—CH$_3$), 1.13 (3H, d, J=7.0 Hz, C$_{6\alpha}$—CH$_3$), 1.47 (3H, s, C$_{19}$—CH$_3$), 2.05 (3H, s, C$_{17}$—COCH$_3$), 2.17 (3H, s, C$_{21}$—COCH$_3$), 4.47 (1H, br, C$_{11}$—CH), 4.81 (2H, d, J=4.5 Hz, C$_{21}$—CH$_2$), 6.01 (1H, s, C$_4$—CH), 6.25 (1H, d, J=10 Hz, C$_2$—CH), 7.27 (1H, d, J=10 Hz, C$_1$—CH).

MS m/e: 459 (M$^+$+1), 458 (M$^+$), 441, 440 (M$^+$−18), 338, 356, 325, 297, 279, 189, 161, 136 (base peak), 135, 121, 43.

Elementary analysis (as C$_{26}$H$_{34}$O$_7$): Calc. (%): C 68.10; H 7.47. Found (%): C 67.91; H 7.21.

EXAMPLE 7

21-Acetoxy-11β-hydroxy-6α-methyl-17α-propionyloxy-1,4-pregnadiene-3,20-dione

In 4 ml of dimethylformamide was dissolved 1.12 g of 6α-methylprednisolone. To this solution were added 1.06 g of ethyl orthopropionate and 0.026 g of p-toluenesulfonic acid, and the mixture was heated with stirring under an argon current at 80° C. for 1.5 hours. Next, 100 ml of ethyl acetate and 0.5 ml of a 10% aqueous solution of sodium carbonate were added to the reaction liquid at room temperature and then 50 ml of water was also added thereto. This mixture was well shaken and the ethyl acetate layer was separated, washed twice with 30 ml of water and dried over anhydrous sodium sulfate. After filtration, the filtrate was concentrated and the resultant crude product was recrystallized from ether whereby 1.28 g (yield: 92.8%) of 6α-methylprednisolone 17α,21-ethyl orthopropionate was obtained as colorless needle crystals. Below are physical properties and various analytical data of this compound.

M.P. 160.0°–164.0° C. (with decomp.).

IR $\nu_{max}^{KBr}$ cm$^{-1}$: 3350 (OH), 1720 (C=O), 1645 (C=O).

MS m/e: 459 (M$^+$+1), 458 (M$^+$), 441, 430, 413, 395, 356, 311, 297, 279, 237, 161, 136, 135 (base peak), 121, 57.

Elementary analysis (as C$_{27}$H$_{38}$O$_6$): Calc. (%): C 70.71; H 8.35. Found (%): C 70.59; H 8.47.

In 8 ml of methanol was dissolved 320 mg of the 6α-methyl-prednisolone 17α,21-ethyl orthopropionate. To this solution was added 1.5 ml of 2N-oxalic acid, and the mixture was heated at 40° C. for 10 minutes. The resultant reaction liquid was concentrated under reduced pressure. To the residue were added successively 50 ml of ethyl acetate, 0.5 ml of a 10% solution of sodium carbonate and 30 ml of water, and the mixture was well shaken. The ethyl acetate layer was separated, dried over anhydrous sodium sulfate and concentrated to obtain a crude product which was then subjected to preparative thin layer chromatography on silica gel whereby 235 mg (yield: 78.3%) of 11β,21-dihydroxy-6α-methyl-17α-propionyloxy-1,4-pregnadiene-3,20-dione was obtained.

In 4 ml of methylene chloride was dissolved 210 mg of this compound. To this solution were added 400 mg of triethylamine and 120 mg of acetic anhydride, and the mixture was stirred for 7 hours at room temperature. To this reaction liquid was then added 1 ml of methanol, and the mixture was stirred for further 2 hours and then concentrated under reduced pressure. The resultant residue was directly subjected to preparative thin layer chromatography (silica gel) for purification and then recrystallized from ether to obtain 187 mg (yield: 80.6%) of the title compound as colorless fine needle crystals. Shown below are physical properties and various analytical data of this compound.

M.P. 129.0°–131.0° C.

TLC (silica gel): Rf 0.37 (single spot; benzene:ethanol=10:1).

IR $\nu_{max}^{KBr}$ cm$^{-1}$: 3380, 1755, 1730, 1650.

NMRδCDCl$_3$: 1.06 (3H, s, C$_{18}$—CH$_3$), 1.15 (3H, d, J=6.0 Hz, C$_{6\alpha}$—CH$_3$), 1.12 (3H, t, J=8 Hz, CH$_2$CH$_3$), 1.48 (3H, s, C$_{19}$—CH$_3$), 2.18 (3H, s, COCH$_3$), 4.52 (1H, br, C$_{11}$—CH), 4.80 (2H, d, J=4.0 Hz, C$_{21}$—CH$_2$), 6.05 (1H, s, C$_4$—CH), 6.28 (1H, d, J=10 Hz, C$_2$—CH), 7.33 (1H, d, J=10 Hz, C$_1$—CH).

MS m/e: 473 (M$^+$+1), 472 (M$^+$), 455, 454, 418, 401, 398, 327, 325, 299, 297, 281, 279, 185, 161, 136, 135, 121, 91, 57 (base peak), 43.

Elementary analysis (as C$_{27}$H$_{36}$O$_7$): Calc. (%): C 68.62; H 7.68. Found (%): C 68.42; H 7.42.

EXAMPLE 8

17α-Acetoxy-21-benzoyloxy-11β-hydroxy-6α-methyl-1,4-pregnadiene-3,20-dione

In 4 ml of methylene chloride was dissolved 208 mg of 17α-acetoxy-11β,21-dihydroxy-6α-methyl-1,4-pregnadiene-3,20-dione obtained according to the method described in Example 6. To this solution was added 202 mg of triethylamine, and the mixture was ice-cooled. Next, 140 mg of benzoyl chloride was directly added to the solution and the mixture was stirred for one hour. To the solution was further added 1 ml of methanol, and the mixture was stirred for one hour. The reaction liquid was concentrated under reduced pressure and the resultant residue was directly subjected to preparative thin layer chromatography (silica gel) for purification whereby 204 mg (yield: 78.5%) of the title compound was obtained as a colorless amorphous solid. The structure of this compound was confirmed by the following physical properties and results of various analyses:

M.P. 135.5°–138.5° C. (as reference).

TLC (silica gel): RF 0.41 (single spot; benzene:ethanol = 10:1).

IR$\nu_{max}^{KBr}$ cm$^{-1}$: 3400, 1735, 1720, 1650.

NMR$\delta$CDCl$_3$: 1.07 (3H, s, C$_{18}$—CH$_3$), 1.12 (3H, d, J=6 Hz, C$_{6\alpha}$—CH$_3$), 1.46 (3H, s, C$_{19}$—CH$_3$), 2.08 (3H, s, COCH$_3$), 4.52 (1H, br, C$_{11}$—CH), 5.00 (2H, d, J=4.0 Hz, C$_{21}$—CH$_2$), 6.00 (1H, s, C$_4$—CH), 6.26 (1H, d, J=10 Hz, C$_2$—CH), 7.26 (1H, d, J=10 Hz, C$_1$—CH), 7.30–8.25 (5H, m, Ph).

MS m/e: 521 (M$^+$+1), 520 (M$^+$), 503, 502, 460, 413, 385, 325, 297, 279, 239, 161, 136, 135, 121, 105 (base peak), 77, 43.

Elementary analysis (as C$_{31}$H$_{36}$O$_7$): Calc. (%): C 71.52; H 6.97. Found (%): C 71.72; H 7.26.

EXAMPLE 9

17α-Acetoxy-11β-hydroxy-6α-methyl-21-propionyloxy-1,4-pregnadiene-3,20-dione

In 4 ml of methylene chloride was dissolved 178 mg of 17α-acetoxy-11β,21-dihydroxy-6α-methyl-1,4-pregnadiene-3,20-dione obtained according to the method described in Example 6. To this solution was added 395 mg of propionic anhydride and 480 mg of pyridine, and the mixture was stirred for 19 hours at room temperature. The reaction liquid was treated as described in Example 6 whereupon 170 mg (yield: 85.0%) of the title compound was obtained as colorless needle crystals. Shown below are physical properties and various analytical data of this compound.

M.P. 161.5°–163.5° C.

TLC (silica gel): Rf 0.38 (single spot; benzene:ethanol = 10:1).

IR$\nu_{max}^{KBr}$ cm$^{-1}$: 3360, 1740, 1725, 1715, 1650.

NMR$\delta$CDCl$_3$: 0.89–1.27 (9H, m, —CH$_2$CH$_3$, C$_{18}$—CH$_3$ and C$_{6\alpha}$—CH$_3$), 1.45 (3H, s, C$_{19}$—CH$_3$), 2.02 (3H, s, —COCH$_3$), 4.50 (1H, br, C$_{11}$—CH), 4.77 (2H, d, J=6Hz, C$_{21}$—CH$_2$), 6.07 (1H, s, C$_4$—CH), 6.31 (1H, d, J=10 Hz, C$_2$—CH), 7.37 (1H, d, J=10Hz, C$_1$—CH).

MS m/e: 473 (M$^+$+1), 472 (M$^+$), 455, 454, 412, 346, 337, 325, 297, 279, 189, 161, 136 (base peak), 135, 121.

Elementary analysis (as C$_{27}$H$_{36}$O$_7$): Calc. (%): C 68.62; H 7.68. Found (%): C 68.57; H 7.73.

EXAMPLE 10

21-Butyryloxy-11β-hydroxy-6α-methyl-17α-propionyloxy-1,4-pregnadiene-3,20-dione

In 4 ml of methylene chloride was dissolved 215 mg of 11β,21-dihydroxy-6α-methyl-17α-propionyloxy-1,4-pregnadiene-3,20-dione obtained according to the method described in Example 7. To this solution were added 404 mg of triethylamine and 316 mg of butyric anhydride, and the mixture was stirred for 18 hours at room temperature. Next, 2 ml of methanol was added to this reaction liquid and the mixture was stirred for further 4 hours. The reaction liquid was concentrated under reduced pressure and the obtained residue was directly subjected to preparative thin layer chromatography (silica gel) for purification and then recrystallized from ether-hexane whereby 203 mg (yield: 81.2%) of the title compound was obtained as colorless platelet crystals. Shown below are physical properties and various analytical data of this compound.

M.P. 112.5°–114.5° C.

TLC (silica gel): Rf 0.40 (single spot; benzene:ethanol = 10:1).

IR$\nu_{max}^{KBr}$ cm$^{-1}$: 3400, 1740, 1730, 1720, 1650.

NMR$\delta$CDCl$_3$: 0.98–1.23 (9H, m, CH$_2$CH$_2$CH$_3$, CH$_2$CH$_3$ and C$_{6\alpha}$—CH$_3$), 1.05 (3H, s, C$_{18}$—CH$_3$), 1.47 (3H, s, C$_{19}$—CH$_3$), 4.51 (1H,br, C$_{11}$—CH), 4.77 (2H, d, J=5.0 Hz, C$_{21}$—CH$_2$), 6.02 (1H, s, C$_4$—CH), 6.27 (1H, d, J=10 Hz, C$_2$—CH), 7.28 (1H, d, J=10 Hz, C$_1$—CH).

MS m/e: 501 (M$^+$+1), 500 (M$^+$), 483, 482, 426, 411, 365, 356, 338, 325, 297, 279, 189, 187, 161, 136 (base peak), 135, 121, 91, 71, 57.

Elementary analysis (as C$_{29}$H$_{40}$O$_7$): Calc. (%): C 69.57; H 8.05. Found (%): C 69.59; H 7.82.

EXAMPLE 11

11β-Hydroxy-21-isobutyryloxy-6α-methyl-17α-propionyloxy-1,4-pregnadiene-3,20-dione In 4 ml of methylene chloride was dissolved 215 mg of 11β,21-dihydroxy-6α-methyl-17α-propionyloxy-1,4-pregnadiene-3,20-dione obtained according to the method as described in Example 7. To this solution were added 348 mg of diethylmethylamine and 316 mg of isobutyric anhydride, and the mixture was stirred for 18 hours at room temperature. Next, 2 ml of methanol was added to the mixture and the whole was stirred for 3 hours. The reaction liquid was concentrated under reduced pressure and the obtained residue was purified by subjecting it directly to preparative thin layer chromatography (silica gel) and recrystallized from ether-hexane whereby 216 mg (yield: 86.4%) of the title compound was obtained as colorless needle crystals. Shown below are physical properties and various analytical data of this compound.

M.P. 144.0°–146.0° C.

TLC (silica gel): Rf 0.41 (single spot; benzene:ethanol = 10:1).

IR$\nu_{max}^{KBr}$ cm$^{-1}$: 3360, 1740, 1730, 1650.

NMR$\delta$CDCl$_3$: 1.06 (3H, s, C$_{18}$—CH$_3$), 1.25 (6H, d, J=6 Hz,

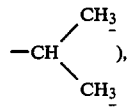

0.97–1.20 (6H, m, CH$_2$CH$_3$ and C$_{6\alpha}$—CH$_3$), 1.47 (3H, s, C$_{19}$—CH$_3$), 4.46 (1H, br, C$_{11}$—CH), 4.76 (2H, d, J=6 Hz, C$_{21}$—CH$_2$), 6.04 (1H, s, C$_4$—CH), 6.27 (1H, d, J=10 Hz, C$_2$—CH), 7.28 (1H, d, J=10 Hz, C$_1$—CH).

MS m/e: 501 (M$^+$+1), 500 (M$^+$), 483, 482, 426, 411, 365, 356, 325, 297, 279, 189, 187, 161, 136 (base peak), 135 121, 91, 71, 57.

Elementary analysis (as C$_{29}$H$_{40}$O$_7$): Calc. (%): C 69.57; H 8.05. Found (%): C 69.63; H 8.16.

EXAMPLE 12

21-Benzoyloxy-11β-hydroxy-6α-methyl-17α-propionyloxy-1,4-pregnadiene-3,20-dione

In 4 ml of methylene chloride was dissolved 235 mg of 11β,21-dihydroxy-6α-methyl-17α-propionyloxy-1,4-pregnadiene-3,20-dione obtained according to the method as described in Example 7. To this solution were added 120 mg of benzoyl chloride and 133 mg of pyridine, and the mixture was stirred for 22 hours at room temperature. The reaction liquid was then treated in the same manner as described in Example 8 whereupon 246 mg (yield: 84.3%) of the title compound was obtained. This compound was a colorless amorphous solid but was comfirmed to be pure in view of its physical properties and results of various analyses shown below.

TLC (silica gel): Rf 0.43 (single spot; benzene:ethanol=10:1).

IR$\nu_{max}^{KBr}$ cm$^{-1}$: 3400, 1730, 1720, 1700, 1650.

NMR$\delta$CDCl$_3$: 1.00–1.23 (9H, m, —CH$_2$CH$_3$, C$_{18}$—CH$_3$ and C$_{6\alpha}$—CH$_3$), 1.45 (3H, s, C$_{19}$—CH$_3$), 4.48 (1H, br, C$_{11}$—CH), 5.00 (2H, d, J=5 Hz, C$_{21}$—CH$_2$), 6.05 (1H, s, C$_4$—CH), 6.28 (1H, d, J=10 Hz, C$_2$—CH), 7.23–8.18 (6H, m, C$_1$—CH and Ph).

MS m/e: 535 (M$^+$+1), 534 (M$^+$), 516, 460, 399, 325, 297, 279 161, 136, 135, 121, 106, 105 (base peak), 77.

Elementary analysis (as C$_{32}$H$_{38}$O$_7$): Calc. (%): C 71.89; H 7.16. Found (%): C 71.72; H 7.30.

EXAMPLE 13

21-Acetoxy-17α-butyryloxy-11β-hydroxy-6α-methyl-1,4-pregnadiene-3,20-dione

In 2 ml of methylene chloride was dissolved 65 mg of 17α-butyryloxy-11β,21-dihydroxy-6α-methyl-1,4-pregnadiene-3,20-dione obtained according to the method as described in Example 1-(a). To this solution were dissolved 0.2 ml of pyridine and 0.2 ml of acetic anhydride, and the mixture was stirred for 6 hours at room temperature. To this mixture was added 2 ml of methanol, and the whole was stirred for further 2 hours. Ethyl acetate (50 ml) was added to the reaction liquid and the mixture was treated in the same manner as described in Example 6 whereupon 56 mg (yield: 78.9%) of the title compound was obtained as colorless fine needle crystals. Shown below are physical properties and various analytical data of this compounds.

M.P. 158.5°–160.5° C.

TLC (silica gel): Rf 0.38 (single spot; benzene:ethanol=10:1).

IR$\nu_{max}^{KBr}$ cm$^{-1}$: 3380, 1755, 1725, 1720, 1650.

NMR$\delta$CDCl$_3$: 0.96 (3H, t, J=7 Hz, CH$_2$CH$_2$CH$_3$), 1.06 (3H, s, C$_{18}$—CH$_3$), 1.15 (3H, d, J=6 Hz, C$_{6\alpha}$—CH$_3$), 1.48 (3H, s, C$_{19}$—CH$_3$), 2.19 (3H, s, COCH$_3$), 4.48 (1H, br, C$_{11}$—CH), 4.79 (2H, d, J=4 Hz, C$_{21}$—CH$_2$), 6.03 (1H, s, C$_4$—CH), 6.26 (1H, d, J=10 Hz, C$_2$—CH), 7.31 (1H, d, J=10 Hz, C$_1$—CH).

MS m/e: 487 (M$^+$+1), 486 (M$^+$), 469, 398, 383, 356, 325, 297, 279, 263, 189, 161, 136 (base peak), 135, 121, 91, 71, 43.

Elementary analysis (as C$_{28}$H$_{38}$O$_7$): Calc. (%): C 69.12; H 7.87. Found (%): C 68.83; H 7.95.

EXAMPLE 14

17α-Butyryloxy-11β-hydroxy-6α-methyl-21-propionyloxy-1,4-pregnadiene-3,20-dione In 2 ml of methylene chloride was dissolved 145 mg of 17α-butyryloxy-11β,21-dihydroxy-6α-methyl-1,4-pregnadiene-3,20-dione obtained according to the method as described in Example 1-(a). To this solution were added 210 mg of pyridine and 150 mg of propionic anhydride, and the mixture was stirred for 24 hours at room temperature. To this reaction liquid was added 50 ml of ethyl acetate, and the liquid mixture was washed successively with 30 ml of water, 10 ml of a 1% solution of sodium carbonate, 30 ml of water, 10 ml of 1% hydrochloric acid and twice 30 ml of water and then dried over anhydrous sodium sulfate. The mixture was filtered and the filtrate was concentrated to obtain a crude product which was then purified by means of preparative thin layer chromatography (silica gel) and recrystallized from acetone-hexane whereby 145 mg (yield: 88.8%) of the title compound was obtained as colorless needle crystals.

M.P. 121.0°–122.5° C.

TLC (silica gel): Rf 0.41 (single spot; benzene:ethanol=10:1).

IR$\nu_{max}^{KBr}$ cm$^{-1}$: 3400, 1740, 1720, 1715, 1650.

NMR$\delta$CDCl$_3$: 1.02 (6H, t, J=7 Hz, CH$_2$CH$_3$x2), 1.02 (3H, s, C$_{18}$—CH$_3$), 1.18 (3H, d, J=6 Hz, C$_{6\alpha}$—CH$_3$), 1.44 (3H, s, C$_{19}$—CH$_3$), 4.48 (1H, br, C$_{11}$—CH), 4.73 (2H, d, J=5 Hz, C$_{21}$—CH$_2$), 6.00 (1H, s, C$_4$—CH), 6.24 (1H, d, J=10 Hz, C$_2$—CH), 7.30 (1H, d, J=10 Hz, C$_1$—CH).

MS m/e: 501 (M$^+$+1), 500 (M$^+$), 482, 413, 325, 297, 279, 161, 136 (base peak), 135, 121.

Elementary analysis (as C$_{29}$H$_{40}$O$_7$): Calc. (%): C 69.57; H 8.05. Found (%): C 69.71; H 8.16.

EXAMPLE 15

17α,21-Dibutyryloxy-11β-hydroxy-6α-methyl-1,4-pregnadiene-3,20-dione

In 2 ml of methylene chloride was dissolved 105 mg of 17α-butyryloxy-11β,21-dihydroxy-6α-methyl-1,4-pregnadiene-3,20-dione obtained according to the method as described in Example 1-(a). To this solution were added 187 mg of butyric anhydride and 186 mg of pyridine, and the mixture was stirred for 24 hours at room temperature. To this reaction liquid was added 50 ml of ethyl acetate, and the ethyl acetate solution was washed successively with 30 ml of water, 2 ml of a 10% solution of sodium carbonate, 30 ml of water, 2 ml of 10% hydrochloric acid and twice 30 ml of water and dried over anhydrous sodium sulfate. The solution was filtered and the filtrate was concentrated to obtain a crude product which was than subjected to preparative thin layer chromatography (silica gel) for purification and then recrystallized from acetone-hexane whereby 115 mg (yield: 95.4%) of the title compound was obtained as colorless needle crystals. Shown below are physical properties and various analytical data of this compound.

M.P. 142.0°–144.0° C.

TLC (silica gel): Rf 0.42 (single spot; benzene:ethanol=10:1).

IR$\nu_{max}^{KBr}$ cm$^{-1}$: 3380, 1740, 1725, 1715, 1650.

NMR$\delta$CDCl$_3$: 0.97 (3H, s, C$_{18}$—CH$_3$), 1.07 (6H, s, —CH$_2$CH$_3$x2), 1.15 (3H, d, J=6 Hz, C$_{6\alpha}$—CH$_3$), 1.48 (3H, s, C$_{19}$—CH$_3$), 4.53 (1H, br, C$_{11}$—CH), 4.80 (2H, d, J=5 Hz, C$_{21}$—CH$_2$), 6.09 (1H, s, C$_4$—CH), 6.32 (1H, d, J=10 Hz, C$_2$—CH), 7.34 (1H, d, J=10 Hz, C$_1$—CH).

MS m/e: 515 (M$^+$+1), 514 (M$^+$), 496, 427, 297, 279, 161, 136 135, 121, 71 (base peak).

Elementary analysis (as C$_{30}$H$_{42}$O$_7$): Calc. (%): C 70.01; H 8.23. Found (%): C 70.18; H 8.43.

EXAMPLE 16

21-Acetoxy-11β-hydroxy-17α-isobutyryloxy-6α-methyl-1,4-pregnadiene-3,20-dione In 4 ml of methylene chloride was dissolved 180 mg of 11β,21-dihydroxy-17α-isobutyryloxy-6α-methyl-1,4-pregnadiene-3,20-dione obtained according to the method as described in Example 2-(a). To this solution were added 200 mg of triethylamine and 120 mg of acetic anhydride, and the mixture was stirred for 7 hours at room temperature. To the reaction liquid was added 2 ml of methanol, and the mixture was stirred for further 2 hours and then concentrated under reduced pressure. The resultant residue was subjected to preparative thin layer chromatography (silica gel) for purification and then recrystallized from ether-hexane whereby 158 mg (yield: 81.0%) of the title compound was obtained as colorless platelet crystals. Shown below are physical properties and various analytical data of this compound.

M.P. 141.5°–143.5° C.

TLC (silica gel): Rf 0.39 (single spot; benzene:ethanol = 10:1).

IR$\nu_{max}^{KBr}$ cm$^{-1}$: 3350, 1750, 1730, 1725, 1650.

NMR$\delta$CDCl$_3$: 1.03 (3H, s, C$_{18}$—CH$_3$), 1.10 (3H, m, C$_{6\alpha}$—CH$_3$), 1.13 (6H, d, J=8 Hz,

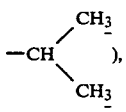

1.43 (3H, s, C$_{19}$—CH$_3$), 2.17 (3H, s, COCH$_3$), 4.50 (1H, br, C$_{11}$—CH), 4.77 (2H, d, J=5 Hz, C$_{21}$—CH$_2$), 6.06 (1H, s, C$_4$—CH), 6.28 (1H, d, J=10 Hz, C$_2$—CH), 7.26 (1H, d, J=10 Hz, C$_1$—CH).

MS m/e: 487 (M$^+$+1), 486 (M$^+$), 469, 468, 413, 398, 351, 325, 297, 279, 263, 161, 136, 135, 121, 91, 71, 43 (base peak).

Elementary analysis (as C$_{28}$H$_{38}$O$_7$): Calc. (%): C 69.11; H 7.87. Found (%): C 68.91; H 8.00.

EXAMPLE 17

17α-Butyryloxy-11β-hydroxy-21-isobutyryloxy-6α-methyl-1,4-pregnadiene-3,20-dione In 4 ml of methylene chloride was dissolved 160 mg of 17α-butyryloxy-11β,21-dihydroxy-6α-methyl-1,4-pregnadiene-3,20-dione obtained according to the method as described in Example 1-(a). To this solution were added 171 mg of isobutyric anhydride and 174 mg of diethylmethylamine, and the mixture was stirred for 18 hours at room temperature. The reaction liquid was concentrated under reduced pressure and the resultant residue was subjected to preparative thin layer chromatography for purification and then recrystallized from ether-hexane whereby 165 mg (yield: 89.2%) of the title compound was obtained as colorless platelet crystals. Shown below are physical properties and various analytical data of this compound.

M.P. 154.5°–156.5° C.

TLC (silica gel): Rf 0.43 (single spot; benzene:ethanol = 10:1).

IR$\nu_{max}^{KBr}$ cm$^{-1}$: 3360, 1740, 1730, 1650.

NMR$\delta$CDCl$_3$: 0.95 (3H, m, CH$_2$CH$_2$CH$_3$), 1.05 (3H, s, C$_{18}$—CH$_3$), 1.23 (6H, d, J=6 Hz,

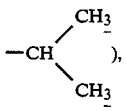

1.10–1.18 (3H, m, C$_{6\alpha}$—CH$_3$), 1.46 (3H, s, C$_{19}$—CH$_3$), 4.52 (1H, br, C$_{11}$—CH), 4.75 (2H, d, J=6 Hz, C$_{21}$—CH$_2$), 6.08 (1H, s, C$_4$—CH), 6.32 (1H, d, J=10 Hz, C$_2$—CH), 7.32 (1H, d, J=10 Hz, C$_4$—CH).

MS m/e: 515 (M$^+$+1), 514 (M$^+$), 497, 496, 426, 379, 356, 325, 309, 297, 279, 205, 189, 187, 161, 136, 135, 121, 91, 71 (base peak).

Elementary analysis (as C$_{30}$H$_{42}$O$_7$): Calc. (%): C 70.01; H 8.23. Found (%): C 70.03; H 8.42.

EXAMPLE 18

11β-Hydroxy-17α-isobutyryloxy-6α-methyl-21-propionyloxy-1,4-pregnadiene-3,20-dione In 5 ml of benzene was dissolved 120 mg of 11β,21-dihydroxy-17α-isobutyryloxy-6α-methyl-1,4-pregnadiene-3,20-dione obtained according to the method as described in Example 2-(a). To this solution were added 130 mg of propionic anhydride and 0.5 ml of pyridine, and the mixture was stirred for 24 hours at room temperature. The reaction mixture was treated in the same manner as described in Example 6 and the resultant crude product was recrystallized from acetone-hexane whereby 120 mg (yield: 88.7%) of the title compound was obtained as colorless needle crystals. Shown below are physical properties and various analytical data of this compound.

M.P. 128.0°–131.0° C.

TLC (silica gel): Rf 0.41 (single spot; benzene:ethanol = 10:1).

IR$\nu_{max}^{KBr}$ cm$^{-1}$: 3390, 1740, 1720, 1710, 1645.

NMR$\delta$CDCl$_3$: 1.08–1.32 (15H, m,

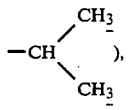

CH$_2$CH$_3$, C$_{18}$—CH$_3$ and C$_{6\alpha}$—CH$_3$), 1.46 (3H, s, C$_{19}$—CH$_3$), 4.52 (1H, br, C$_{11}$—CH), 4.88 (2H, d, J=6Hz, C$_{21}$—CH$_2$), 6.00 (1H, s, C$_4$—CH), 6.23 (1H, d, J=10 Hz, C$_2$—CH), 7.28 (1H, d, J=10 Hz, C$_1$—CH).

MS m/e: 501 (M$^+$+1), 500 (M$^+$), 482 (M$^+$−18), 413, 297, 279, 161, 136 (base peak), 135, 121.

Elementary analysis (as C$_{29}$H$_{40}$O$_7$): Calc. (%): C 69.57; H 8.05. Found (%): C 69.72; H 8.09.

EXAMPLE 19

11β-Hydroxy-17α,21-diisobutyryloxy-6α-methyl-1,4-pregnadiene-3,20-dione

In 5 ml of benzene was dissolved 222 mg of 11β,21-dihydroxy-17α-isobutyryloxy-6α-methyl-1,4-pregnadiene-3,20-dione obtained according to the method as described in Example 2-(a). To this solution were added 237 mg of isobutyric anhydride and 0.5 ml of pyridine, and the mixture was stirred for 24 hours at room temperature. The reaction liquid was treated in the same manner as described in Example 6 and 171 mg (yield: 66.4%) of the title compound was obtained as colorless needle crystals. Shown below are physical properties and various analytical data of this compound.

M.P. 165.6°–166.5° C.

TLC (silica gel): Rf 0.43 (single spot; benzene:ethanol = 10:1).

IR$\nu_{max}^{KBr}$ cm$^{-1}$: 3350, 1740, 1720, 1710, 1645.

NMR$\delta$CDCl$_3$: 1.05–1.27 (18H, m,

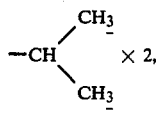

$C_{18}$—$CH_3$ and $C_{6\alpha}$—$CH_3$), 1.46 (3H, s, $C_{19}$—$CH_3$), 4.46 (1H, br, $C_{11}$—CH), 4.75 (2H, d, J=8 Hz, $C_{21}$—$CH_2$), 6.02 (1H, s, $C_4$—CH), 6.27 (1H, d, J=10 Hz, $C_2$—CH), 7.30 (1H, d, J=10 Hz, $C_1$—CH).

MS m/e: 515 (M$^+$+1), 514 (M$^+$), 496, 427, 297, 279, 161, 136 (base peak), 135, 121.

Elementary analysis (as $C_{30}H_{42}O_7$): Calc. (%): C 70.01; H 8.23. Found (%): C 70.16; H 8.21.

EXAMPLE 20

21-Acetoxy-11β-hydroxy-6α-methyl-17α-valeryloxy-1,4-pregnadiene-3,20-dione

In 4 ml of methylene chloride were dissolved 147 mg of 11β,21-dihydroxy-6α-methyl-17α-valeryloxy-1,4-pregnadiene-3,20-dione obtained according to the method as described in Example 3. To this solution were added 200 mg of triethylamine and 102 mg of acetic anhydride, and the mixture was stirred for 8 hours at room temperature. To the reaction liquid was added 1 ml of methanol, and the mixture was stirred for further 2 hours. The reaction liquid was concentrated under reduced pressure and the resultant residue was subjected to preparative thin layer chromatography (silica gel) for purification and then recrystallized from ether-hexane whereby 132 mg (yield: 82.5%) of the title compound was obtained as needle crystals. Shown below are physical properties and various analytical data of this compound.

M.P. 175.0°–177.0° C.

TLC (silica gel): Rf 0.40 (single spot; benzene:ethanol=10:1).

IR$\nu_{max}^{KBr}$ cm$^{-1}$: 3300, 1755, 1730, 1720, 1650.

NMRδCDCl$_3$: 0.91–1.25 (3H, m, $CH_2CH_2CH_2CH_3$), 1.02 (3H, s, $C_{18}$—$CH_3$), 1.12 (3H, d, J=7 Hz, $C_{6\alpha}$—$CH_3$), 1.48 (3H, s, $C_{19}$—$CH_3$), 2.17 (3H, s, COCH$_3$), 4.49 (1H, br, $C_{11}$—CH), 4.78 (2H, d, J=4 Hz, $C_{21}$—$CH_2$), 6.03 (1H, s, $C_4$—CH), 6.27 (1H, d, J=10 Hz, $C_2$—CH), 7.29 (1H, d, J=10 Hz, $C_1$—CH).

MS m/e: 501 (M$^+$+1), 500 (M$^+$), 482, 427, 398, 365, 325, 297, 279, 263, 189, 161, 136 (base peak), 135, 121, 91, 85, 73, 59, 57, 43.

Elementary analysis (as $C_{29}H_{40}O_7$): Calc. (%): C 69.57; H 8.05. Found (%): C 69.43; H 8.15.

EXAMPLE 21

21-Butyryloxy-11β-hydroxy-17α-isobutyryloxy-6α-methyl-1,4-pregnadiene-3,20-dione In 4 ml of methylene chloride were dissolved 180 mg of 11β,21-dihydroxy-17α-isobutyryloxy-6α-methyl-1,4-pregnadiene-3,20-dione obtained according to the method as described in Example 2-(a). To this solution were added 200 mg of triethylamine and 158 mg of butyric anhydride, and the mixture was stirred for 20 hours at room temperature. To the reaction liquid was added 1 ml of methanol, and the mixture was stirred for further 2 hours. The reaction liquid was concentrated under reduced pressure and the resultant residue was subjected to preparative thin layer chromatography for purification and then recrystallized from ether-hexane whereby 168 mg (yield: 81.6%) of the title compound was obtained as colorless platelet crystals. Shown below are physical properties and various analytical data of this compound.

M.P. 121.0°–123.5° C.

TLC (silica gel): Rf 0.43 (single spot; benzene:ethanol=10:1).

IR$\nu_{max}^{KBr}$ cm$^{-1}$: 3400, 1745, 1730, 1650.

NMRδCDCl$_3$: 1.00 (3H, m, $CH_2CH_2CH_3$), 1.06 (3H, s, $C_{18}$—$CH_3$), 1.14 (3H, m, $C_{6\alpha}$—$CH_3$), 1.16 (6H, d, J=7 Hz,

1.48 (3H, s, $C_{19}$—$CH_3$), 4.51 (1H, br, $C_{11}$—CH), 4.75 (2H, d, J=6.5 Hz, $C_{21}$—$CH_2$), 6.03 (1H, s, $C_4$—CH), 6.29 (1H, d, J=10 Hz, $C_2$—CH), 7.29 (1H, d, J=10 Hz, $C_1$—CH).

MS m/e: 515 (M$^+$+1), 514 (M$^+$), 497, 496, 426, 413, 379, 356, 325, 297, 279, 221, 205, 189, 161, 136, 135, 121, 91, 71, 43 (base peak).

Elementary analysis (as $C_{30}H_{42}O_7$): Calc. (%): C 70.01; H 8.23. Found (%): C 69.95; H 8.14.

EXAMPLE 22

11β-Hydroxy-17α-isovaleryloxy-6α-methyl-21-propionyloxy-1,4-pregnadiene-3,20-dione In 5 ml of benzene was dissolved 310 mg of 11β,21-dihydroxy-17α-isovaleryloxy-6α-methyl-1,4-pregnadiene-3,20-dione obtained according to the method as described in Example 4. To this solution were added 240 mg of propionic anhydride and 0.5 ml of pyridine, and the mixture was stirred for 20 hours at room temperature. The reaction liquid was treated in the same manner as described in Example 6 whereby 279 mg (yield: 80.1%) of the title compound was obtained as colorless needle crystals. Shown below are physical properties and various analytical data of this compound.

M.P. 163.5°–164.5° C.

TLC (silica gel): Rf 0.43 (single spot; benzene:ethanol=10:1).

IR$\nu_{max}^{KBr}$ cm$^{-1}$: 3360, 1740, 1720, 1710, 1645.

NMRδCDCl$_3$: 0.90–1.20 (15H, m,

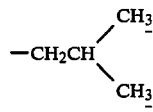

—$CH_2CH_3$, $C_{18}$—$CH_3$ and $C_{6\alpha}$—$CH_3$), 1.42 (3H, s, $C_{19}$—$CH_3$), 4.47 (1H, br, $C_{11}$—CH), 4.77 (2H, d, J=4 Hz, $C_{21}$—$CH_2$), 6.03 (1H, s, $C_4$—CH), 6.26 (1H, d, J=10 Hz, $C_2$—CH), 7.33 (1H, d, J=10 Hz, $C_1$—CH).

MS m/e: 515 (M$^+$+1), 514 (M$^+$), 499, 356, 325, 297, 279, 161, 136 (base peak), 135, 121.

Elementary analysis (as $C_{30}H_{42}O_7$): Calc. (%): C 70.01; H 8.23. Found (%): C 70.23; H 8.45.

EXAMPLE 23

11β-Hydroxy-6α-methyl-21-propionyloxy-17α-valeryloxy-1,4-pregnadiene-3,20-dione

In 3 ml of methylene chloride was dissolved 176 mg of 11β,21-dihydroxy-6α-methyl-17α-valeryloxy-1,4-pregnadiene-3,20-dione. To this solution were added 316 mg of pyridine and 250 mg of propionic anhydride, and the mixture was stirred for 24 hours at room temperature. Next, 50 ml of ethyl acetate was added to the reaction liquid and the liquid mixture was washed successively with 30 ml of water, 1 ml of a 10% solution of sodium carbonate, 30 ml of water, 2 ml of 10% HCl and 30 ml of water and then dried over anhydrous sodium sulfate. After filtration of the liquid mixture, the filtrate was concentrated and the resultant residue was subjected to preparative thin layer chromatography (silica gel) for purification whereby 165 mg (yield: 83.3%) of the title compound was obtained as colorless needle crystals. Shown below are physical properties and various analytical data of this compound.

M.P. 183.0°–184.0° C.

TLC (silica gel): Rf 0.42 (single spot; benzene:ethanol=10:1).

IR$\nu_{max}^{KBr}$ cm$^{-1}$: 360, 1740, 1720, 1645.

NMR$\delta$CDCl$_3$: 1.00 (6H, t, J=8 Hz, CH$_2$CH$_3\times$2), 1.00 (3H, s, C$_{18}$—CH$_3$), 1.16 (3H, d, J=6 Hz, C$_{6\alpha}$—CH$_3$), 1.42 (3H, s, C$_{19}$—CH$_3$), 4.47 (1H, br, C$_{11}$—CH), 4.78 (2H, d, J=5 Hz, C$_{21}$—CH$_2$), 6.00 (1H, s, C$_4$—CH), 6.23 (1H, d, J=10 Hz, C$_2$—CH), 7.30 (1H, d, J=10 Hz, C$_1$—CH).

MS m/e: 505 (M$^+$+1), 514 (M$^+$), 496 (M$^+$−18), 297, 279, 161, 136 (base peak), 135, 121.

Elementary analysis (as C$_{30}$H$_{42}$O$_7$): Calc. (%): C 70.01; H 8.23. Found (%): C 69.88; H 8.41.

EXAMPLE 24

21-Acetoxy-11β-hydroxy-17α-isovaleryloxy-6α-methyl-1,4-pregnadiene-3,20-dione

In 4 ml of methylene chloride was dissolved 92 mg of 11β,21-dihydroxy-17α-isovaleryloxy-6α-methyl-1,4-pregnadiene-3,20-dione. To this solution were added 200 mg of triethylamine and 102 mg of acetic anhydride, and the mixture was stirred for 8 hours at room temperature. To the reaction liquid was added 1 ml of methanol, and the mixture was stirred for further 2 hours. The reaction liquid was concentrated under reduced pressure and the resultant residue was subjected to preparative thin layer chromatography (silica gel) for purification and then recrystallized from ether-hexane whereby 87 mg (yield: 87.0%) of the title compound was obtained as colorless needle crystals. Shown below are physical properties and various analytical data of this compound.

M.P. 178.5°–180.5° C.

TLC (silica gel): Rf 0.39 (single spot; benzene:ethanol=10:1).

IR$\nu_{max}^{KBr}$ cm$^{-1}$: 3340, 1750, 1730, 1720, 1650.

NMR$\delta$CDCl$_3$: 0.91 (3H, m, C$_{18}$—CH$_3$), 1.01 (6H, d, J=3 Hz,

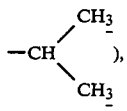

1.12 (3H, d, J=7 Hz), C$_{6\alpha}$—CH$_3$), 1.45 (3H, s, C$_{19}$—CH$_3$), 2.15 (3H, s, COCH$_3$), 4.46 (1H, m, C$_{11}$—CH), 4.76 (2H, d, J=3.5 Hz, C$_{21}$—CH$_2$), 6.02 (1H, s, C$_4$—CH), 6.26 (1H, d, J=10 Hz, C$_2$—CH), 7.27 (1H, d, J=10 Hz, C$_1$—CH).

MS m/e: 501 (M$^+$+1), 500 (M$^+$), 483, 427, 398, 365, 325, 315, 297, 279, 263, 189, 187, 161, 136 (base peak), 135 121, 91, 85, 57, 43.

Elementary analysis (as C$_{28}$H$_{38}$O$_7$): Calc. (%): C 69.12; H 7.87. Found (%): C 69.33; H 8.14.

EXAMPLE 25

17α-Acetoxy-11β-hydroxy-6α-methyl-21-valeryloxy-1,4-pregnadiene-3,20-dione

In 4 ml of methylene chloride was dissolved 208 mg of 17α-acetoxy-11β,21-dihydroxy-6α-methyl-1,4-pregnadiene-3,20-dione obtained according to the method as described in Example 6. To this solution was added 0.5 ml of pyridine, and the mixture was ice-cooled. To the mixture was added slowly a solution of 241 mg of valeryl chloride in 2 ml of methylene chloride, and the mixture was stirred for one hour. To this reaction liquid was added 60 ml of ethyl acetate, and the mixture was washed successively with 30 ml of water, 10 ml of a dilute aqueous solution of sodium carbonate, 30 ml of water, 5 ml of dilute hydrochloric acid and twice 30 ml of water and dried over anhydrous sodium sulfate. After filtration, the filtrate was concentrated and the resultant residue was subjected to preparative thin layer chromatography (silica gel) for purification whereby 186 mg (yield: 87.4%) of the title compound was obtained as colorless needle crystals (recrystallized from ether-hexane). Shown below are physical properties and various analytical data of this compound.

M.P. 148.0°–150.0° C.

TLC (silica gel): Rf 0.42 (single spot; benzene:ethanol=10:1).

IR$\nu_{max}^{KBr}$ cm$^{-1}$: 3360, 1750, 1730, 1650.

NMR$\delta$CDCl$_3$: 0.93 (3H, m, CH$_2$CH$_2$CH$_2$CH$_3$), 1.03 (3H, s, C$_{18}$—CH$_3$), 1.12 (3H, d, J=7 Hz, C$_{6\alpha}$—CH$_3$), 1.46 (3H, s, C$_{19}$—CH$_3$), 2.05 (3H, s, COCH$_3$), 4.49 (1H, br, C$_{11}$—CH), 4.76 (2H, d, J=4 Hz, C$_{21}$—CH$_2$), 6.03 (1H, s, C$_4$—CH), 6.27 (1H, d, J=10 Hz, C$_2$—CH), 7.29 (1H, d, J=10 Hz, C$_1$—CH).

MS m/e: 501 (M$^+$+1), 500 (M$^+$), 483 (M$^+$−17), 482 (M$^+$−18), 440, 425, 356, 325, 297, 279, 189, 161, 136 (base peak), 135, 121, 85, 57, 43.

Elementary analysis (as C$_{29}$H$_{40}$O$_7$): Calc. (%): C 69.57; H 8.05. Found (%): C 69.60; H 8.15.

EXAMPLE 26

17α-Acetoxy-11β-hydroxy-21-isovaleryloxy-6α-methyl-1,4-pregnadiene-3,20-dione

In 4 ml of methylene chloride was dissolved 208 mg of 11β,21-dihydroxy-17α-acetoxy-6α-methyl-1,4-pregnadiene-3,20-dione obtained according to the method as described in Example 6. To this solution was added 202 mg of triethylamine and the solution was cooled externally with ice. To this solution was added slowly a solution of 120 mg of isovaleryl chloride in 1 ml of methylene chloride, and the mixture was stirred for 1.5 hours. To the reaction liquid was added 1 ml of methanol, and the mixture was further stirred for one hour. The reaction liquid was concentrated under reduced pressure and the resultant residue was directly subjected to preparative thin layer chromatography (silica gel) for purification and then recrystallized from ether-hexane whereby 195 mg (yield: 78.0%) of the title compound was obtained as colorless fine needle crystals. Shown below are physical properties and various analytical data of this compound.

M.P. 126.5°–129.5° C.

TLC (silica gel): Rf 0.41 (single spot; benzene:ethanol=10:1).

IR$\nu_{max}^{KBr}$ cm$^{-1}$: 3400, 1740, 1730, 1650.

NMRδCDCl₃: 0.92 (3H, s, C₁₈—CH₃), 1.03 (6H, s-like,

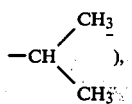

10.8 (3H, d, J=6 Hz, C₆α—CH₃), 1.45 (3H, s, C₁₉—CH₃), 2.02 (3H, s, COCH₃), 4.49 (1H, br, C₁₁—CH), 4.76 (2H, d, J=4 Hz, C₂₁—CH₂), 6.02 (1H, s, C₄—CH), 6.26 (1H, d, J=10 Hz, C₂—CH), 7.29 (1H, d, J=10 Hz, C₁—CH).

MS m/e: 501 (M⁺+1), 500 (M⁺), 483, 482, 440, 425, 356, 325, 297, 279, 189, 161, 136 (base peak), 135, 121, 85, 57, 43.

Elementary analysis (as C₂₉H₄₀O₇): Calc. (%): C 69.57; H 8.05. Found (%): C 69.46; H 8.10.

EXAMPLE 27

11β-Hydroxy-6α-methyl-17α-propionyloxy-21-valeryloxy-1,4-pregnadiene-3,20-dione

In 4 ml of methylene chloride was dissolved 215 mg of 11β,21-dihydroxy-6α-methyl-17α-propionyloxy-1,4-pregnadiene-3,20-dione obtained according to the method as described in Example 7. To this solution was added 348 mg of diethylmethylamine, and the mixture was cooled externally with ice. To the solution was slowly added 240 mg of valeryl chloride, and the mixture was stirred for 1.5 hours. To the reaction liquid was added 2 ml of methanol, and the mixture was further stirred for 2 hours. The reaction liquid was concentrated under reduced pressure and the resultant residue was subjected directly to preparative thin layer chromatography (silica gel) for purification and then recrystallized from ether-hexane whereby 204 mg (yield: 79.4%) of the title compound was obtained as colorless platelet crystals. Shown below are physical properties and various analytical data of this compound.

M.P. 141.5°-143.0° C.

TLC (silica gel): Rf 0.43 (single spot; benzene:ethanol=10:1).

IRν$_{max}^{KBr}$ cm⁻¹: 3400, 1745, 1730, 1655.

NMRδCDCl₃: 0.94-1.25 (6H, m, CH₂CH₃ and CH₂CH₂CH₂CH₃), 1.07 (3H, s, C₁₈—CH₃), 1.14 (3H, d, J=6 Hz, C₆α—CH₃), 1.48 (3H, s, C₁₉—CH₃), 4.49 (1H, br, C₁₁—CH), 4.79 (2H, d, J=4 Hz, C₂₁—CH₂), 6.03 (1H, s, C₄—CH), 6.28 (1H, d, J=10 Hz, C₂—CH), 7.32 (1H, d, J=10 Hz, C₁—CH).

MS m/e: 515 (M⁺+1), 514 (M⁺), 497, 496, 440, 425, 399, 379, 356, 338, 297, 279, 189, 187, 161, 136 (base peak), 135, 91, 85, 57.

Elementary analysis (as C₃₀H₄₂O₇): Calc. (%): C 70.01; H 8.23. Found (%): C 69.79; H 8.07.

EXAMPLE 28

11β-Hydroxy-21-isovaleryloxy-6α-methyl-17α-propionyloxy-1,4-pregnadiene-3,20-dione In 4 ml of methylene chloride was dissolved 215 mg of 11β,21-dihydroxy-6α-methyl-17α-propionyloxy-1,4-pregnadiene-3,20-dione obtained according to the method as described in Example 7. To this solution was added 202 mg of triethylamine, and the mixture was stirred under external ice-cooling. To this solution was added slowly 120 mg of isovaleryl chloride, and the mixture was stirred for one hour. After the addition of 1 ml of methanol, the mixture was further stirred for one hour. The reaction liquid was concentrated under reduced pressure and the resultant residue was subjected directly to preparative thin layer chromatography (silica gel) for purification and then recrystallized from ether-hexane whereby 211 mg (yield: 82.1%) of the title compound was obtained as colorless platelet crystals. Shown below are physical properties and various analytical data of this compound.

M.P. 124.5°-126.0° C.

TLC (silica gel): Rf 0.42 (single spot; benzene:ethanol=10:1).

IRν$_{max}^{KBr}$ cm⁻¹: 3380, 1740, 1730, 1650.

NMRδCDCl₃: 0.93 (3H, s, C₁₈—CH₃), 0.95-1.21 (6H, m, C₆α—CH₃ and CH₂CH₃), 1.02 (6H, s,

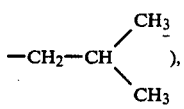

1.48 (3H, s, C₁₉—CH₃), 4.48 (1H, br, C₁₁—CH), 4.76 (2H, d, J=6 Hz, C₂₁—CH₂), 6.01 (1H, s, C₄—CH), 6.25 (1H, d, J=10 Hz, C₂—CH), 7.30 (1H, d, J=10 Hz, C₁—CH).

MS m/e: 515 (M⁺+1), 514 (M⁺), 497, 496, 440, 425, 399, 379, 356, 338, 325, 297, 279, 189, 187, 161, 136 (base peak), 135, 121, 91, 85, 57.

Elementary analysis (as C₃₀H₄₂O₇): Calc. (%): C 70.01; H 8.23. Found (%): C 69.86; H 8.35.

EXAMPLE 29

11β-Hydroxy-21-methoxyacetoxy-6α-methyl-17α-propionyloxy-1,4-pregnadiene-3,20-dione In 4 ml of methylene chloride was dissolved 215 mg of 11β,21-dihydroxy-6α-methyl-17α-propionyloxy-1,4-pregnadiene-3,20-dione. To this solution were added 180 mg of methoxyacetic acid and 412 mg of N,N'-dicyclohexylcarbodiimide, and the mixture was stirred for 48 hours at room temperature. The solvent was distilled off and 50 ml of ethyl acetate was added to the residue. The mixture was washed with 2 ml of a dilute aqueous solution of Na₂CO₃ and 20 ml of water. The ethyl acetate layer was washed twice with 20 ml of water, dried over anhydrous sodium sulfate and then filtered. The filtrate was concentrated and the resultant residue was subjected to preparative thin layer chromatography whereby 184 mg (yield: 73.3%) of the title compound was obtained. This compound was a colorless amorphous solid but its structure was confirmed as a result of the following analyses:

IRν$_{max}^{KBr}$ cm⁻¹: 3440 (OH), 1760, 1730, 1720, 1655.

NMRδCDCl₃: 1.06 (3H, s, C₁₈—CH₃), 1.20 (3H, t, J=7.0 Hz, —CH₂CH₃), 1.22 (3H, d, J=6 Hz, C₆α—CH₃), 1.46 (3H, s, C₁₉—CH₃), 3.48 (3H, s, OCH₃), 4.20 (2H, s, COCH₂O).

MS m/e: 503 (M⁺+1), 502 (M⁺), 484, 428, 297, 279, 136 (base peak), 135, 91, 74, 73, 57, 45.

Elementary analysis (as C₂₈H₃₈O₈): Calc. (%): C 66.91; H 7.62. Found (%): C 67.17; H 7.53.

EXAMPLE 30

17α-Butyryloxy-11β-hydroxy-21-methoxyacetoxy-6α-methyl-1,4-pregnadiene-3,20-dione Using 222 mg of 17α-butyryloxy-11β,21-dihydroxy-6α-methyl-1,4-pregnadiene-3,20-dione obtained according to the method as described in Example 1-(a), the reaction with methoxyacetic acid was carried out in the same manner as described in Example 29 and the after-treatment was also carried out similarly to obtain the title compound. This crude product was then recrystallized from ether-hexane to give 179 mg (yield: 69.4%) of the pure product as colorless needle crystals.

M.P. 1115.20–113.0° C.

IR$\nu_{max}^{KBr}$ cm$^{-1}$: 3400 (OH), 1760, 1745, 1725, 1650.

NMR$\delta$CDCl$_3$: 0.92–1.08 (3H, m, CH$_2$CH$_2$CH$_3$), 1.04 (3H, s, C$_{18}$—CH$_3$), 1.10 (3H, d, J=6 Hz, C$_{6\alpha}$—CH$_3$), 1.44 (3H, s, C$_{19}$—CH$_3$), 3.48 (3H, s, OCH$_3$), 4.18 (2H, s, COCH$_2$O).

MS m/e: 517 (M$^+$+1), 516 (M$^+$), 499, 498, 325, 297, 279, 161, 136 (base peak), 135, 121, 91, 71, 45.

Elementary analysis (as C$_{29}$H$_{40}$O$_8$): Calc. (%): C 67.42; H 7.80. Found (%): C 67.37; H 7.85.

EXAMPLE 31

11$\beta$-Hydroxy-17$\alpha$-isobutyryloxy-21-methoxyacetoxy-6$\alpha$-methyl-1,4-pregnadiene-3,20-dione Using 215 mg of 11$\beta$,21-dihydroxy-17$\alpha$-isobutyryloxy-6$\alpha$-methyl-1,4-pregnadiene-3,20-dione obtained according to the method as described in Example 2-(a), the reaction with methoxyacetic acid was carried out in the same manner as described in Example 29 and the after-treatment was also carried out similarly to obtain the title compound. This crude product was recrystallized from ether-hexane to give 192 mg (yield: 77.4%) of the pure product.

M.P. 119.0°–121.0° C.

IR$\nu_{max}^{KBr}$ cm$^{-1}$: 3420 (OH), 1760, 1730, 1715, 1655.

NMR$\delta$CDCl$_3$: 1.07 (3H, s, C$_{18}$—CH$_3$), 1.12 (6H, d, J=8 Hz, CH(CH$_3$)$_2$), 1.48 (3H, s, C$_{19}$—CH$_3$), 3.47 (3H, s, OCH$_3$), 4.17 (2H, COCH$_2$O).

MS m/e: 517 (M$^+$+1), 516 (M$^+$), 498, 427, 325, 297, 279, 161, 136 (base peak), 135, 73, 71, 45.

Elementary analysis (as C$_{29}$H$_{40}$O$_8$): Calc. (%): C 67.42; H 7.80. Found (%): C 67.28; H 7.93.

EXAMPLE 32

11$\beta$,21-Dihydroxy-17$\alpha$-methoxyacetoxy-6$\alpha$-methyl-1,4-pregnadiene-3,20-dione In 4 ml of dimethylformamide was dissolved 748 mg of 6$\alpha$-methylprednisolone. To this solution was added 768 mg of ethyl orthomethoxyacetate, and the mixture was heated at 75° C. under an argon current. To the reaction liquid was then added 17 mg of anhydrous p-toluenesulfonic acid, and the mixture was stirred for 2 hours at the same temperature. The reaction mixture was then treated in the same manner as described in Example 1-(a) whereby 826 mg (yield: 87.1%) of 6$\alpha$-methylprednisolone 17$\alpha$,21-ethyl orthomethoxyacetate was obtained as colorless needle crystals. This compound was a mixture of its stereoisomers.

The ethyl orthomethoxyacetate used in this Example was obtained by reacting methoxyacetonitrile with hydrogen chloride in dry ethanol and then treating the resultant ethyl iminoether hydrochloride with ethanol. B.P. 177.0°–180.0° C.

In 8 ml of methanol was dissolved 237 mg of the above 6$\alpha$-methylprednisolone 17$\alpha$,21-ethyl orthomethoxyacetate. To this solution was 1 ml of 2N-oxalic acid, and the mixture was warmed at 40° C. for 10 minutes. The solvent was removed by distillation under reduced pressure and the residue was treated in the same manner as described in Example 1-(b) whereby 138 mg (yield: 61.9%) of the title compound was obtained as a colorless amorphous solid. The structure of this compound was confirmed by the following analytical results:

IR$\nu_{max}^{KBr}$ cm$^{-1}$: 3420 (OH), 1740, 1720, 1655.

NMR$\delta$CDCl$_3$: 1.10 (3H, s, C$_{18}$—CH$_3$), 1.26 (3H, d, J=6 Hz, C$_{6\alpha}$—CH$_3$), 1.47 (3H, s, C$_{19}$—CH$_3$), 3.39 (3H, s, OCH$_3$), 4.00 (2H, s, COCH$_2$O), 4.35 (2H, s, C$_{21}$—CH$_2$), 4.51 (1H, br.s, C$_{11}$—CH), 6.08 (1H, s, C$_4$—CH), 6.33 (1H, d, J=10 Hz, C$_2$—CH), 7.26 (1H, d, J=10Hz, C$_1$—CH).

MS m/e: 447 (M$^+$+1), 446 (M$^+$), 428, 357, 298, 161, 136 (base peak), 135, 121, 45.

Elementary analysis (as C$_{25}$H$_{34}$O$_7$): Calc. (%): C 67.25; H 7.67. Found (%): C 67.01; H 7.81.

EXAMPLE 33

21-Acetoxy-11$\beta$-hydroxy-17$\alpha$-methoxyacetoxy-6$\alpha$-methyl-1,4-pregnadiene-3,20-dione In 4 ml of methylene chloride was dissolved 223 mg of 11$\beta$,21-dihydroxy-17$\alpha$-methoxyacetoxy-6$\alpha$-methyl-1,4-pregnadiene-3,20-dione obtained according to the method as described in Example 32. To this solution were added 404 mg of triethylamine and 204 mg of acetic anhydride, and the mixture was stirred for 5 hours at room temperature. The reaction mixture was then treated in the same manner as described in Example 7 whereby 186 mg (yield: 76.2%) of the title compound was obtained as colorless needle crystals.

M.P. 149.5°–151.5° C.

IR$\nu_{max}^{KBr}$ cm$^{-1}$: 3320 (OH), 1760, 1730, 1720, 1655.

NMR$\delta$CDCl$_3$: 1.05 (3H, s, C$_{18}$—CH$_3$), 1.13 (3H, d, J=6 Hz, C$_{6\alpha}$—CH$_3$), 1.48 (3H, s, C$_{19}$—CH$_3$), 2.14 (3H, s, COCH$_3$), 3.42 (3H, s, OCH$_3$), 3.99 (2H, s, COCH$_2$O).

MS m/e: 489 (M$^+$+1), 488 (M$^+$), 470, 398, 325, 297, 279, 161, 136 (base peak), 135, 121, 45, 43.

Elementary analysis (as C$_{27}$H$_{36}$O$_8$): Calc. (%): C 66.38; H 7.43. Found (%): C 66.30; H 7.56.

EXAMPLE 34

11$\beta$-Hydroxy-17$\alpha$-methoxyacetoxy-6$\alpha$-methyl-21-propionyloxy-1,4-pregnadiene-3,20-dione In 2 ml of methylene chloride was dissolved 223 mg of 11$\beta$,21-dihydroxy-17$\alpha$-methoxyacetoxy-6$\alpha$-methyl-1,4-pregnadiene-3,20-dione obtained according to the method as described in Example 32. To this solution were added 404 mg of triethylamine and 208 mg of propionic anhydride, and the mixture was stirred for 5 hours at room temperature. The reaction mixture was then treated in the same manner as described in Example 7 whereby 157 mg (yield: 62.5%) of the title compound was obtained as colorless needle crystals.

M.P. 114.5°–116.5° C.

IR$\nu_{max}^{KBr}$ cm$^{-1}$: 3420 (OH), 1750, 1740–1730, 1655.

NMR$\delta$CDCl$_3$: 1.06 (3H, s, C$_{18}$—CH$_3$), 1.17 (3H, m, CH$_2$CH$_3$), 1.22 (3H, d, J=6 Hz, C$_{6\alpha}$—CH$_3$), 1.47 (3H, s, C$_{19}$—CH$_3$), 3.40 (3H, s, OCH$_3$), 4.00 (2H, s, COCH$_2$O).

MS m/e: 503 (M$^+$+1), 502 (M$^+$), 484, 412, 398, 325, 297, 279, 161, 136 (base peak), 135, 121, 57, 45.

Elementary analysis (as C$_{28}$H$_{38}$O$_8$): Calc. (%): C 66.91; H 7.62. Found (%): C 67.13; H 7.58.

EXAMPLE 35

21-Butyryloxy-11$\beta$-hydroxy-17$\alpha$-methoxyacetoxy-6$\alpha$-methyl-1,4-pregnadiene-3,20-dione In 2 ml of methylene chloride was dissolved 223 mg of 11$\beta$,21-dihydroxy-17$\alpha$-methoxyacetoxy-6$\alpha$-methyl- 1,4-pregnadiene-3,20-dione obtained according to the method as described in Example 32. To this solution were added 404 mg of triethylamine and 253 mg of butyric anhydride, and the mixture was stirred for 5 hours at room temperature. The reaction mixture was then treated in the same manner as described in Example 7 whereby 178 mg (yield: 69.0%) of the title compound was obtained as colorless needle crystals.

M.P. 132.0°–133.5° C.

IR$\nu_{max}^{KBr}$ cm$^{-1}$: 3340 (OH), 1745, 1740–1730, 1655.

NMRδCDCl$_3$: 1.10 (3H, s, C$_{18}$—CH$_3$), 1.15 (3H, m, CH$_2$CH$_3$), 1.47 (3H, s, C$_{19}$—CH$_3$), 3.42 (3H, s, OCH$_3$), 4.00 (2H, s, COCH$_2$O).

MS m/e: 517 (M$^+$+1), 516 (M$^+$), 498 (M$^+$−18), 426, 412, 356, 297, 279, 136 (base peak), 135, 121, 71, 45.

Elementary analysis (as C$_{29}$H$_{40}$O$_8$): Calc. (%): C 67.42; H 7.80. Found (%): C 67.48; H 7.71.

EXAMPLE 36

11β-Hydroxy-21-isobutyryloxy-17α-methoxyacetoxy-6α-methyl-1,4-pregnadiene-3,20-dione In 2 ml of methylene chloride was dissolved 223 mg of 11β,21-dihydroxy-17α-methoxyacetoxy-6α-methyl-1,4-pregnadiene-3,20-dione obtained according to the method as described in Example 32. To this solution were added 404 mg of triethylamine and 253 mg of isobutyric anhydride, and the mixture was stirred for 5 hours at room temperature. The reaction mixture was then treated in the same manner as described in Example 7 whereby 168 mg (yield: 65.1%) of the title compound was obtained as colorless needle crystals.

M.P. 148.0°–149.5° C.

IR$\nu_{max}^{KBr}$ cm$^{-1}$: 3400 (OH), 1750, 1740–1730, 1655.

NMRδCDCl$_3$: 1.10 (3H, s, C$_{18}$—CH$_3$), 1.23 (6H, d, J=7 Hz, CH(CH$_3$)$_2$), 1.48 (3H, s, C$_{19}$—CH$_3$), 3.42 (3H, s, OCH$_3$), 4.01 (2H, s, COCH$_2$O).

MS m/e: 517 (M$^+$+1), 516 (M$^+$), 498, 426, 325, 297, 279, 136 (base peak), 135, 121, 71, 45.

Elementary analysis (as C$_{29}$H$_{40}$O$_8$): Calc. (%): C 67.42; H 7.80. Found (%): C 67.28; H 7.97.

EXAMPLE 37

11β-Hydroxy-17α,21-di(methoxyacetoxy)-6α-methyl-1,4-pregnadiene-3,20-dione

In 4 ml of methylene chloride was dissolved 223 mg of 1β,21-dihydroxy-17α-methoxyacetoxy-6α-methyl-1,4-pregnadiene-3,20-dione obtained according to the method as described in Example 32. To this solution were added 216 mg of methoxyacetic acid and 453 mg of N,N'-dicyclohexylcarbodiimide, and the mixture was stirred for 46 hours at room temperature. The reaction mixture was then treated in the same manner as described in Example 29 whereby 157 mg (yield: 60.6%) of the title compound was obtained. This compound was a colorless amorphous solid but its structure was confirmed by the following analytical results:

IR$\nu_{max}^{KBr}$ cm$^{-1}$: 3340 (OH), 1760, 1745, 1730, 1655.

NMRδCDCl$_3$: 1.06 (3H, s, C$_{18}$—CH$_3$), 1.12 (3H, d, J=6 Hz, C$_{6\alpha}$—CH$_3$), 1.43 (3H, s, C$_{19}$—CH$_3$), 3.42 (3H, s, C$_{17}$—OCOCH$_2$OCH$_3$), 3.49 (3H, s, C$_{21}$—OCOCH$_2$OCH$_3$), 4.00 (2H, s, C$_{17}$—OCOCH$_2$), 4.20 (2H, s, C$_{21}$—OCOCH$_2$).

MS m/e: 519 (M$^+$+1), 518 (M$^+$), 500, 428, 325, 297, 279, 161 136 (base peak), 135, 121, 60, 45.

Elementary analysis (as C$_{28}$H$_{38}$O$_9$): Calc. (%): C 64.85; H 7.39. Found (%): C 64.91; H 7.27.

EXAMPLE 38

11β-Hydroxy-6α-methyl-21-methylthioacetoxy-17α-propionyloxy-1,4-pregnadiene-3,20-dione In 4 ml of methylene chloride was dissolved 235 mg of 11β,21-dihydroxy-6α-methyl-17α-propionyloxy-1,4-pregnadiene-3,20-dione obtained according to the method as described in Example 7. To this solution were added 202 mg of triethylamine and 266 mg of methylthioacetic anhydride, and the mixture was stirred for one hour at room temperature. The reaction mixture was then treated in the same manner as described in Example 7 whereby 207 mg (yield: 72.6%) of the title compound was obtained as colorless needle crystals.

M.P. 126.0°–127.5° C.

IR$\nu_{max}^{KBr}$ cm$^{-1}$: 3400 (OH), 1745, 1730, 1715, 1650.

NMRδCDCl$_3$: 1.06 (3H, s, C$_{18}$—CH$_3$), 1.12 (3H, t, J=8 Hz, CH$_2$CH$_3$) 1.46 (3H, s, C$_{19}$—CH$_3$), 2.25 (3H, s, SCH$_3$), 3.31 (2H, s, COCH$_2$S).

MS m/e: 519 (M$^+$+1), 518 (M$^+$), 426, 356, 325, 297, 279, 161, 136 135, 121, 61 (base peak), 57.

Elementary analysis (as C$_{28}$H$_{38}$O$_7$S): Calc. (%): C 64.84; H 7.38. Found (%): C 64.63; H 7.31.

EXAMPLE 39

17α-Butyryloxy-11β-hydroxy-6α-methyl-21-methylthioacetoxy-1,4-pregnadiene-3,20-dione Using 335 mg of 17α-butyryloxy-11β,21-dihydroxy-6α-methyl-1,4-pregnadiene-3,20-dione obtained according to the method as described in Example 1-(a), the reaction with methylthioacetic anhydride was carried out in the same manner as described in Example 38, and the reaction mixture was treated in the same manner as described in Example 7 whereby 294 mg (yield: 73.7%) of the title compound was obtained as colorless needle crystals.

M.P. 173.0°–174.0° C.

IR$\nu_{max}^{KBr}$ cm$^{-1}$: 3360, 1740, 1720, 1710, 1650.

NMRδCDCl$_3$: 1.07 (3H, s, C$_{18}$—CH$_3$), 1.48 (3H, s, C$_{19}$—CH$_3$), 2.25 (3H, s, SCH$_3$), 3.34 (2H, s, COCH$_2$S).

MS m/e: 533 (M$^+$+1), 532 (M$^+$), 443, 429, 425, 397, 325, 297, 279, 161, 136, 135, 121, 71, 61 (base peak).

Elementary analysis (as C$_{29}$H$_{40}$O$_7$S): Calc. (%): C 65.39; H 7.57. Found (%): C 65.52; H 7.55.

EXAMPLE 40

11β-Hydroxy-17α-isobutyryloxy-6α-methyl-21-methylthioacetoxy-1,4-pregnadiene-3,20-dione Using 80 mg of 11β,21-dihydroxy-17α-isobutyryloxy-6α-methyl-1,4-pregnadiene-3,20-dione obtained according to the method as described in Example 2-(a), the reaction with methylthioacetic anhydride was carried out in the same manner as described in Example 38, and the reaction mixture was treated in the same manner as described in Example 7 whereby 86 mg (yield: 89.6%) of the title compund was obtained as colorless needle crystals.

M.P. 136.0°–138.0° C.

IR$\nu_{max}^{KBr}$ cm$^{-1}$: 3320, 1750, 1730, 1710, 1650.

NMRδCDCl$_3$: 1.05 (3H, s, C$_{18}$—CH$_3$), 1.12 (6H, d, J=8 Hz, CH(CH$_3$)$_2$), 1.46 (3H, s, C$_{19}$—CH$_3$), 2.25 (3H, s, SCH$_3$), 3.31 (2H, s, COCH$_2$S).

MS m/e: 533 (M$^+$+1), 532 (M$^+$), 429, 325, 297, 279, 161, 136, 135, 121, 71, 6 (base peak).

Elementary analysis (as C$_{29}$H$_{40}$O$_7$S): Calc. (%): C 65.39; H 7.57. Found (%): C 65.26; H 7.65.

EXAMPLE 41

11β-Hydroxy-17α-methoxyacetoxy-6α-methyl-21-methylthioacetoxy-1,4-pregnadiene-3,20-dione

Using 150 mg of 11β,21-dihydroxy-17α-methoxyacetoxy-6α-methyl-1,4-pregnadiene-3,20-dione obtained according to the method as described in Example 32, the reaction with methylthioacetic anhydride was carried out in the same manner as described in Example 38 and the reaction mixture was treated in the same manner as described in Example 7 whereby 123 mg (yield: 68.3%) of the title compound was obtained as a colorless amorphous solid. The structure of this compound was confirmed by the following analytical results:

$IR\nu_{max}^{KBr}$ cm$^{-1}$: 3420, 1745, 1730, 1720, 1655.

NMRδCDCl$_3$: 1.10 (3H, s, C$_{18}$—CH$_3$), 1.22 (3H, d, J=6 Hz, C$_{6\alpha}$—CH$_3$), 1.48 (3H, s, C$_{19}$—CH$_3$), 2.28 (3H, s, SCH$_3$), 3.37 (2H, s, COCH$_2$S), 3.46 (3H, s, OCH$_3$), 4.03 (2H, s, COCH$_2$O).

MS m/e: 535 (M$^+$+1), 534 (M$^+$), 445, 356, 325, 297, 279, 161, 136, 135, 121, 61, 45 (base peak).

Elementary analysis (as C$_{28}$H$_{38}$O$_8$S): Calc. (%): C 62.90; H 7.16. Found (%): C 63.04; H 7.09.

EXAMPLE 42

11β,21-Dihydroxy-6α-methyl-17α-methylthioacetoxy-1,4-pregnadiene-3,20-dione

In 8 ml of dimethylformamide was dissolved 1.88 g of 6α-methylprednisolone. To this solution was added 1.6 g of ethyl orthomethylthioacetate, and the mixture was heated at 75° C. under an argon current. To this reaction liquid was then added 43 mg of anhydrous p-toluenesulfonic acid, and the mixture was stirred for one hour at the same temperature. The reaction mixture was then treated in the same manner as described in Example 1-(a) whereby 2.15 g (yield: 87.8%) of 6α-methylprednisolone 17α,21-ethyl orthomethylthioacetate was obtained as colorless needle crystals.

M.P. 184.0°-186.0° C.

$IR\nu_{max}^{KBr}$ cm$^{-1}$: 3560, 1715, 1660.

NMRδCDCl$_3$: 0.87 (3H, s, C$_{18}$—CH$_3$), 1.10 (3H, t, J=7 Hz, CH$_2$CH$_3$), 1.12 (3H, d, J=6 Hz, C$_{6\alpha}$—CH$_3$), 1.47 (3H, s, C$_{19}$—CH$_3$), 2.16 (3H, s, SCH$_3$), 2.84 (2H, s,COCH$_2$SCH$_3$), 3.57 (2H, q, J=7 Hz, CH$_2$CH$_3$).

MS m/e: 491 (M$^+$+1), 490 (M$^+$), 445, 429, 357, 297, 279, 161 136, 135 (base peak), 121, 61.

Elmentary analysis (as C$_{27}$H$_{38}$O$_6$S): Calc. (%): C 66.09; H 7.81. Found (%): C 66.13; H 7.75.

To 6 ml of methanol was dissolved 210 mg of the above 6α-methylprednisolone 17α,21-ethyl orthomethylthioacetate. To this solution was added 0.5 ml of 2N-oxalic acid, and the mixture was stirred for 10 minutes at 40° C. The solvent was removed by distillation under reduced pressure and the residue was treated in the same manner as described in Example 1-(b) whereby 143 mg (yield: 71.9%) of the title compound was obtained as a colorless amorphous solid. The structure of this compound was confirmed by the following analytical results:

$IR\nu_{max}^{KBr}$ cm$^{-1}$: 3440, 1720, 1715, 1650.

NMRδCDCl$_3$: 0.98 (3H, s, C$_{18}$—CH$_3$), 1.12 (3H, d, J=6 Hz, C$_{6\alpha}$—CH$_3$), 1.48 (3H, s, C$_{19}$—CH$_3$), 2.16 (3H, s, SCH$_3$), 3.15 (2H, s, COCH$_2$S).

MS m/e: 463 (M$^+$+1), 462 (M$^+$), 444, 431, 356, 325, 297, 279, 161, 136, 135, 121, 91, 61 (base peak).

Elementary analysis (as C$_{25}$H$_{34}$O$_6$S): Calc. (%): C 64.91; H 7.44. Found (%): C 65.03; H 7.38.

EXAMPLE 43

11β-Hydroxy-21-methoxyacetoxy-6α-methyl-17α-methylthioacetoxy-1,4-pregnadiene-3,20-dione

In 4 ml of methylene chloride was dissolved 180 mg of 11β,21-dihydroxy-6α-methyl-17α-methylthioacetoxy-1,4-pregnadiene-3,20-dione obtained according to the method as described in Exampel 42. To this solution were added methoxyacetic anhydride prepared separately from methoxyacetic acid and then triethylamine, and the mixture was stirred for one hour at room temperature. The reaction mixture was then treated in the same manner as described in Example 7 whereby 259 mg (yield: 89.6%) of the title compound was obtained as colorless needle crystals.

M.P. 112.0°-114.0° C.

$IR\nu_{max}^{KBr}$ cm$^{-1}$: 3360, 1760, 1740, 1720, 1650.

NMRδCDCl$_3$: 1.07 (3H, s, C$_{18}$—CH$_3$), 1.28 (3H, d, J=6.5 Hz, C$_{6\alpha}$—CH$_3$), 1.49 (3H, s, C$_{19}$—CH$_3$), 2.18 (3H, s, SCH$_3$), 3.13 (2H, s, COCH$_2$S), 3.47 (3H, s, COCH$_2$OCH$_3$), 4.20 (2H, s, COCH$_2$OCH$_3$).

MS m/e: 535 (M$^+$+1), 534 (M$^+$), 517, 516, 427, 413, 325, 297, 293, 279, 161, 136, 135, 121, 91, 61 (base peak), 45.

Elementary analysis (as C$_{28}$H$_{38}$O$_8$S): Calc. (%): C 62.90; H 7.16. Found (%): C 62.82; H 7.25.

EXAMPLE 44

11β-Hydroxy-6α-methyl-17α,21-di(methylthioacetoxy)-1,4-pregnadiene-3,20-dione

Using 250 mg of 11β,21-dihydroxy-6α-methyl-17α-methylthioacetoxy-1,4-pregnadiene-3,20-dione obtained according to the method as described in Example 42, the reaction with methylthioacetic anhydride was carried out in the same manner as described in Example 38 and the reaction mixture was treated in the same manner as described in Example 7 whereby 215 mg (yield: 72.4%) of the title compound was obtained as colorless needle crystals.

M.P. 175.0°-177.0° C.

$IR\nu_{max}^{KBr}$ cm$^{-1}$: 3370, 1740, 1725, 1720, 1655.

NMRδCDCl$_3$: 1.06 (3H, s, C$_{18}$—CH$_3$), 1.15 (3H, d, J=4 Hz, C$_{6\alpha}$—CH$_3$), 1.47 (3H, s, C$_{19}$—CH$_3$), 2.19 (3H, s, C$_{17}$—OCOCH$_2$SCH$_3$), 2.25 (3H, s, C$_{21}$—OCOCH$_2$SCH$_3$), 3.12 (2H, s, C$_{17}$—OCOCH$_2$S), 3.33 (2H, s, C$_{21}$—OCOCH$_2$S).

MS m/e: 551 (M$^+$+1), 550 (M$^+$), 444, 426, 356, 325, 297, 279, 161, 136, 135, 121, 61 (base peak).

Elementary analysis (as C$_{28}$H$_{38}$O$_7$S$_2$): Calc. (%): C 61.07; H 6.95. Found (%): C 61.22; H 6.82.

EXAMPLE 45

21-Acetoxy-11β-hydroxy-6α-methyl-17α-thioacetoxy-1,4-pregnadiene-3,20-dione

Using 232 mg of 11β,21-dihydroxy-6α-methyl-17α-methylthioacetoxy-1,4-pregnadiene-3,20-dione obtained according to the method as described in Example 42, the reaction with acetic anhydride was carried out in the same manner as described in Example 7 and the reaction mixture was treated similarly whereby 213 mg (yield: 84.5%) of the title compound was obtained as colorless needle crystals.

M.P. 149.0°-151.0° C.

$IR\nu_{max}^{KBr}$ cm$^{-1}$: 3400, 1760, 1725, 1720, 1650.

NMRδCDCl₃: 1.03 (3H, s, C₁₈—CH₃), 1.10 (3H, d, J=8 Hz, C₆α—CH₃), 1.47 (3H, s, C₁₉—CH₃), 2.15 (3H, s, SCH₃), 2.19 (3H, s, COCH₃), 3.12 (2H, s, COCH₂S).

MS m/e: 505 (M⁺+1), 504 (M⁺), 356, 325, 297, 279, 161, 136 135, 121, 61 (base peak), 43.

Elementary analysis (as C₂₇H₃₆O₇S): Calc. (%): C 64.26; H 7.19. Found (%): C 64.47; H 7.14.

EXAMPLE 46

11β-Hydroxy-6α-methyl-17α-methylthioacetoxy-21-propionyloxy-1,4-pregnadiene-3,20-dione Using 232 mg of 11β,21-dihydroxy-6α-methyl-17α-methylthioacetoxy-1,4-pregnadiene-3,20-dione obtained according to the method as described in Example 42, the reaction with propionic anhydride was carried out in the same manner as described in Example 18 with exception that triethylamine was used instead of pyridine, and the reaction mixture was treated in the same manner as described in Example 7 whereby 224 mg (yield: 86.5%) of the title compound was obtained as colorless needle crystals.

M.P. 117.0°–119.0° C.

IRν$_{max}^{KBr}$ cm⁻¹: 3400, 1745, 1725, 1715, 1650.

NMRδCDCl₃: 1.02 (3H, s, C₁₈—CH₃), 1.15 (3H, t, J=8 Hz, CH₂CH₃), 1.45 (3H, s, C₁₉—CH₃), 2.16 (3H, s, SCH₃), 3.12 (2H, s, COCH₂S).

MS m/e: 519 (M⁺+1), 518 (M⁺), 500, 325, 297, 279, 161, 136 135, 121, 91, 61 (base peak), 57.

Elementary analysis (as C₂₈H₃₈O₇S): Calc. (%): C 64.84; H 7.38. Found (%): C 64.92; H 7.61.

EXAMPLE 47

21-Butyryloxy-11β-hydroxy-6α-methyl-17α-methylthioacetoxy-1,4-pregnadiene-3,20-dione Using 232 mg of 11β,21-dihydroxy-6α-methyl-17α-methylthioacetoxy-1,4-pregnadiene-3,20-dione obtained according to the method as described in Example 42, the reaction with butyric anhydride was carried out in the same manner as described in Example 10 and the reaction mixture was treated similarly whereby 231 mg (yield: 86.8%) of the title compound was obtained.

M.P. 126.0°–128.0° C.

IRν$_{max}^{KBr}$ cm⁻¹: 3380, 1745, 1725, 1715, 1650.

NMRδCDCl₃: 1.00 (3H, s, C₁₈—CH₃), 1.02 (3H, t, J=8 Hz, CH₂CH₂CH₃), 1.44 (3H, s, C₁₉—CH₃), 2.18 (3H, s, SCH₃), 3.10 (2H, s, COCH₂S).

MS m/e: 533 (M⁺+1), 532 (M⁺), 514, 325, 297, 279, 161, 136, 135, 121, 91, 71, 61 (base peak).

Elementary analysis (as C₂₉H₄₀O₇S): Calc. (%): C 65.39; H 7.57. Found (%): C 65.51; H 7.30.

EXAMPLE 48

11β-Hydroxy-21-isobutyryloxy-6α-methyl-17α-methylthioacetoxy-1,4-pregnadiene-3,20-dione Using 232 mg of 11β,21-dihydroxy-6α-methyl-17α-methylthioacetoxy-1,4-pregnadiene-3,20-dione, the reaction with isobutyric anhydride was carried out in the same manner as described in Example 11 and the reaction mixture was treated similarly whereby 224 mg (yield: 84.2%) of the title compound was obtained as colorless needle crystals.

M.P. 151.0°–152.0° C.

IRν$_{max}^{KBr}$ cm⁻¹: 3360, 1745, 1725, 1715, 1650.

NMRδCDCl₃: 1.02 (3H, s, C₁₈—CH₃), 1.22 (6H, d, J=7 Hz, CH(CH₃)₂), 1.44 (3H, s, C₁₉—CH₃), 2.18 (3H, s, SCH₃), 3.10 (2H, s, COCH₂S).

MS m/e: 533 (M⁺+1), 532 (M⁺), 514, 356, 325, 297, 279, 161, 136, 135, 121, 91, 71, 61 (base peak).

Elementary analysis (as C₂₉H₄₀O₇S): Calc. (%): C 65.39; H 7.57. Found (%): C 65.47; H 7.49.

It is understood that the preceding representative examples may be varied within the scope of the present specification, both as to reactants and reaction conditions, by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A 6α-methylprednisolone derivative which is a 21-acyloxy-11β-hydroxy-6α-methyl-17α- methyl- or -ethyl-thioacetoxy-1,4-pregnadiene-3,20-dione compound of the formula:

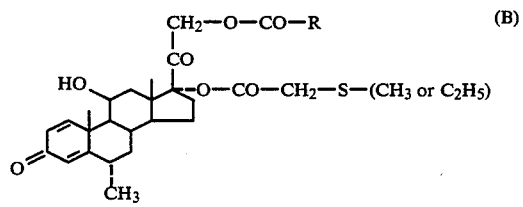

wherein R is a straight or once-branched chain C₁–C₄ alkyl group or a C₁–C₄ alkoxy- or alkylthio-methyl group.

2. A 6α-methylprednisolone derivative according to claim 1, which is a 17α-methylthioacetoxy-21-acyloxy-11β-hydroxy-6α-methyl-1,4-pregnadiene-3,20-dione compound selected from the group consisting of:

17α-methylthioacetoxy-21-acetoxy-11β-hydroxy-6α-methyl-1,4-pregnadiene-3,20-dione, 17α-methylthioacetoxy-21-propionyloxy-11β-hydroxy-6α-methyl-1,4-pregnadiene-3,20-dione, 17α-methylthioacetoxy-21-butyryloxy-11β-hydroxy-6α-methyl-1,4-pregnadiene-3,20-dione, 17α-methylthioacetoxy-21-isobutyryloxy-11β-hydroxy-6α-methyl-1,4-pregnadiene-3,20-dione, 17α-methylthioacetoxy-21-methoxyacetoxy-11β-hydroxy-6α-methyl-1,4-pregnadiene-3,20-dione and 17α,21-di(methylthioacetoxy)-11β-hydroxy-6α-methyl-1,4-pregnadiene-3,20-dione.

3. A 6α-methylprednisolone derivative which is a 17α-acyloxy-11β-hydroxy-6α-methyl-21-methythioacetoxy-1,4-pregnadiene-3,20-dione compund of the formula:

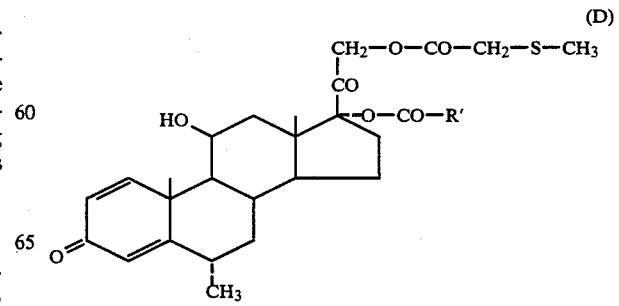

wherein R' is a straight or once-branched chain $C_1$–$C_4$ alkyl group.

4. A 6α-methylprednisolone derivative according to claim 3, which is a 17α-acyloxy-11α-hydroxy-6α-methyl-21-methylthioacetoxy-1,4-pregnadiene-3,20-dione compound selected from the group consisting of:
17α-propionyloxy-21-methylthioacetoxy-11β-hydroxy-6α-methyl-1,4-pregnadiene-3,20-dione,
17α-butyryloxy-21-methylthioacetoxy-11β-hydroxy-6α-methyl-1,4-pregnadiene-3,20-dione and
17α-isobutyryloxy-21-methylthioacetoxy-11β-hydroxy-6α-methyl-1,4-pregnadiene-3,20-dione.

5. A pharmaceutical preparation comprising an effective anti-inflammatory amount of a compound according to claim 1 and a pharmaceutically acceptable carrier or excipient.

6. A pharmaceutical preparation comprising an effective anti-inflammatory amount of a compound according to claim 2 and a pharmaceutically acceptable carrier or excipient.

7. A pharmaceutical preparation comprising an effective anti-inflammatory amount of a compound according to claim 3 and a pharmaceutically acceptable carrier or excipient.

8. A pharmaceutical preparation comprising an effective anti-inflammatory amount of a compound according to claim 4 and a pharmaceutically acceptable carrier or excipient.

9. A method for treating inflammatory conditions comprising administering an effective anti-inflammatory amount of a compound according to claim 1.

10. A method for treating inflammatory conditions comprising administering an effective anti-inflammatory amount of a compound according to claim 2.

11. A method for treating inflammatory conditions comprising administering an effective anti-inflammatory amount of a compound according to claim 3.

12. A method for treating inflammatory conditions comprising administering an effective anti-inflammatory amount of a compound according to claim 4.

* * * * *